US006616686B2

(12) United States Patent
Coleman et al.

(10) Patent No.: US 6,616,686 B2
(45) Date of Patent: Sep. 9, 2003

(54) SURGICAL STAPLES AND METHODS FOR STAPLING

(76) Inventors: James Coleman, 20 Greenmount Road, Terenure, Dublin 6 (IE); Christy Cummins, 54 Knockowen, Tullamore, County Offaly (IE); Chris Martin, 2 Blackburn Square, Rathfarnham, Dublin 14 (IE); Thomas Anthony, 49 Grange Downs, Rathfarnham, Dublin 14 (IE); Sean Morris, Kiltoom, Athlone, County Roseommon (IE)

( * ) Notice: Subject to any disclaimer, the term of this patent is extended or adjusted under 35 U.S.C. 154(b) by 0 days.

(21) Appl. No.: 09/949,438

(22) Filed: Sep. 7, 2001

(65) Prior Publication Data

US 2002/0049472 A1 Apr. 25, 2002

(30) Foreign Application Priority Data

Sep. 8, 2000 (IE) .......................................... S2000/0724
Sep. 8, 2000 (IE) .......................................... S2000/0722

(51) Int. Cl.[7] ............................................ A61B 17/064
(52) U.S. Cl. ........................ 606/219; 606/221; 606/75; 227/175.1
(58) Field of Search .................... 606/75, 219, 220, 606/221, 151, 153; 227/175.1, 180.1

(56) References Cited

U.S. PATENT DOCUMENTS

| | | | |
|---|---|---|---|
| 2,684,070 A | * 7/1954 | Kelsey | .......... 606/221 |
| 3,482,428 A | 12/1969 | Kapitanov et al. | |
| 4,014,492 A | 3/1977 | Rothfuss | |
| 4,428,376 A | * 1/1984 | Mericle | .......... 606/219 |
| 4,523,695 A | 6/1985 | Braun et al. | |
| 4,724,840 A | 2/1988 | McVay et al. | |
| 4,771,782 A | 9/1988 | Millar | |
| 4,789,090 A | 12/1988 | Blake, III | |
| 4,887,601 A | * 12/1989 | Richards | .......... 606/219 |
| 5,147,381 A | 9/1992 | Heimerl et al. | |
| 5,292,309 A | 3/1994 | Van Tassel et al. | |
| 5,292,332 A | 3/1994 | Lee | |
| 5,366,479 A | * 11/1994 | McGarry et al. | .......... 606/219 |
| 5,395,030 A | 3/1995 | Kuramoto et al. | |
| 5,431,639 A | 7/1995 | Shaw | |

(List continued on next page.)

FOREIGN PATENT DOCUMENTS

| | | | |
|---|---|---|---|
| EP | 0 386 361 | | 9/1990 |
| EP | 0386361 A1 | * | 9/1990 |
| EP | 0 756 851 | | 2/1997 |
| EP | 0 774 237 | | 5/1997 |
| EP | 0 941 697 | | 9/1999 |
| FR | 2 443 238 | | 7/1980 |
| GB | 1 358 466 | | 7/1974 |
| WO | WO 97/20505 | | 6/1997 |
| WO | WO 98/17179 | * | 4/1998 |
| WO | WO 98/25508 | | 6/1998 |

*Primary Examiner*—Michael J. Milano
*Assistant Examiner*—Bradford C Pantuck
(74) *Attorney, Agent, or Firm*—Nutter, McClennen & Fish LLP

(57) ABSTRACT

A surgical staple is provided having a base portion and a respective leg extending from each end of the base portion and terminating at a free end. The base portion is deformable to bring the free ends of the legs together to penetrate a liquid-carrying vessel at the site of a puncture and hold the opposite edges of the puncture together. The base portion and legs lie in substantially a common plane except for a center portion (40C) of the base portion which is deformed in a loop in a direction perpendicular to the common plane. The center portion of the staple allows the staple to straddle a blood locator tube projecting from the end of a stapler, so that the staple can be closed at the center of a puncture wound in which the tube is located. A method for stapling is also provided.

27 Claims, 25 Drawing Sheets

U.S. PATENT DOCUMENTS

| | | |
|---|---|---|
| 5,470,010 A | 11/1995 | Rothfuss et al. |
| 5,527,322 A | 6/1996 | Klein et al. |
| 5,536,251 A * | 7/1996 | Evard et al. ............. 604/93.01 |
| 5,560,532 A | 10/1996 | DeFonzo et al. |
| 5,643,318 A | 7/1997 | Tsukernik et al. |
| 5,674,231 A | 10/1997 | Green et al. |
| 5,810,846 A | 9/1998 | Virnich et al. |
| 5,855,312 A | 1/1999 | Toledano |
| 5,861,005 A | 1/1999 | Kontos |

* cited by examiner

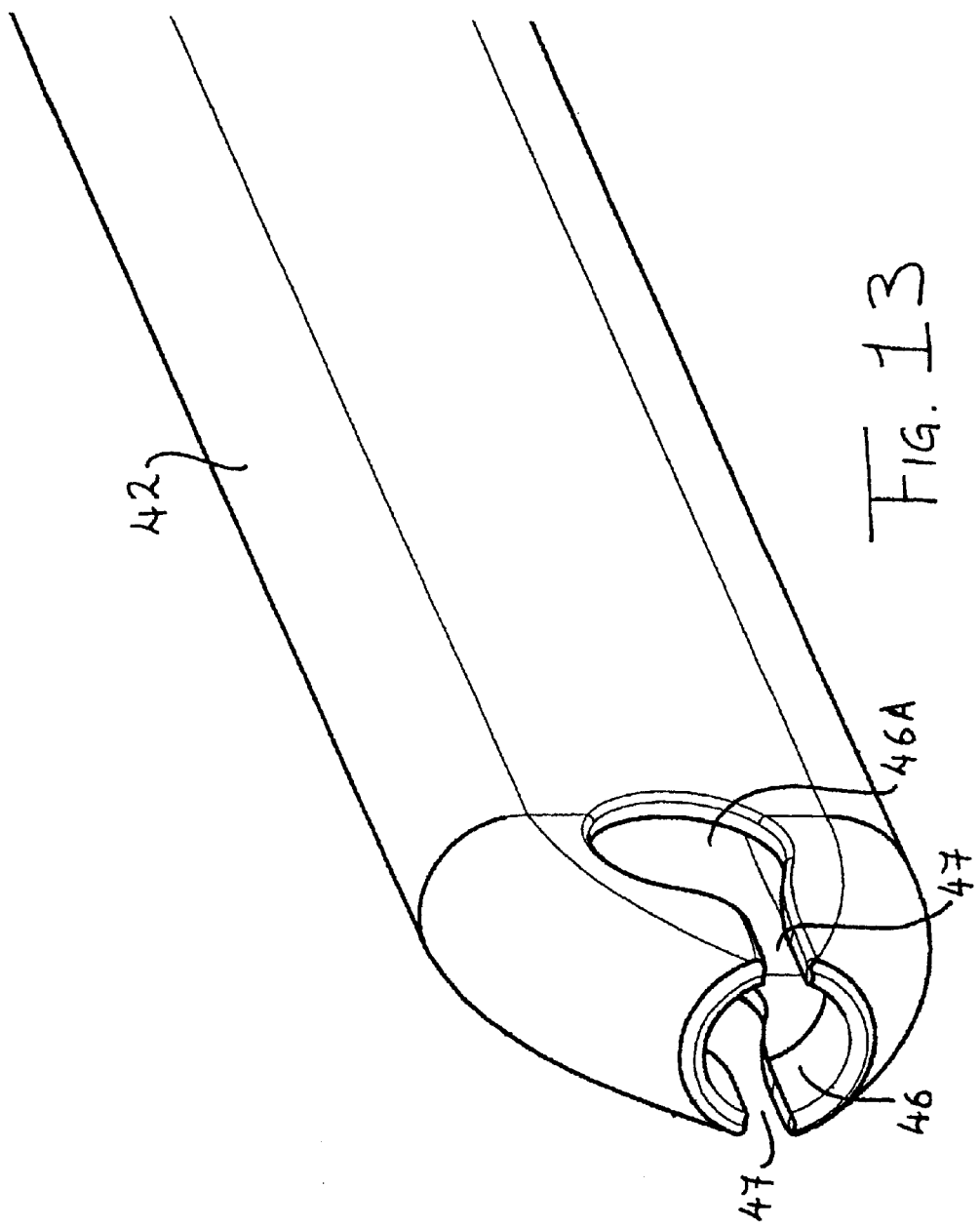

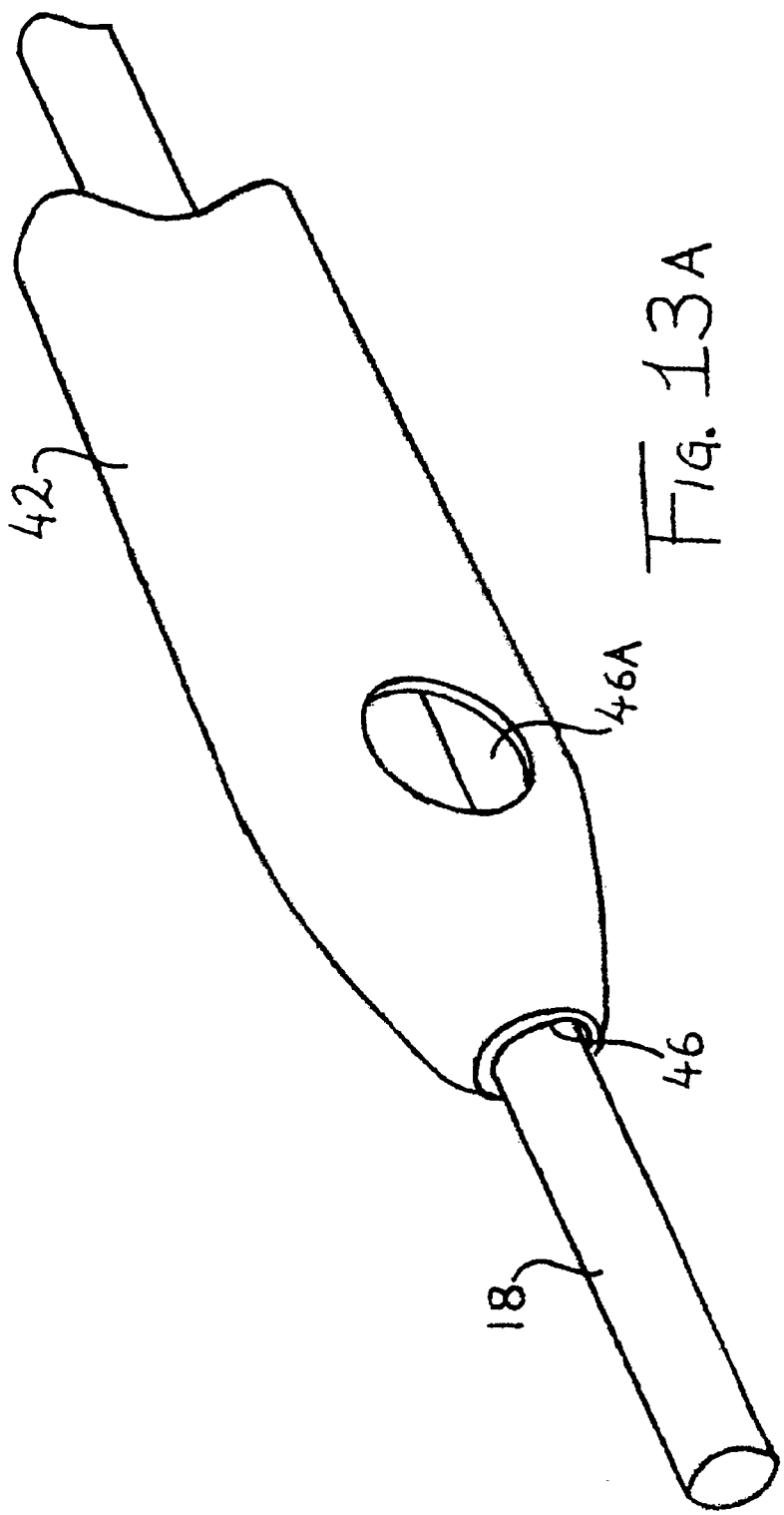

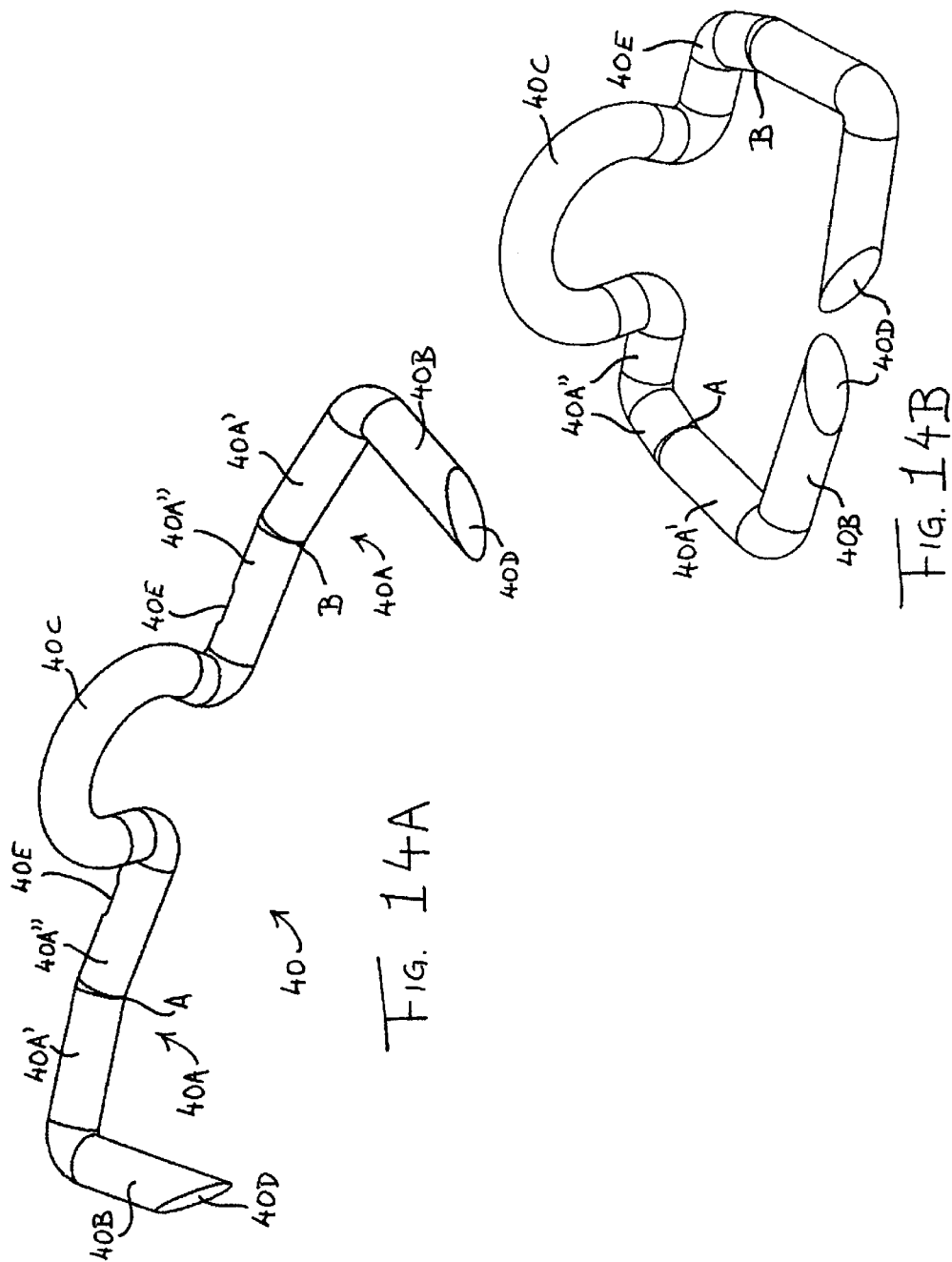

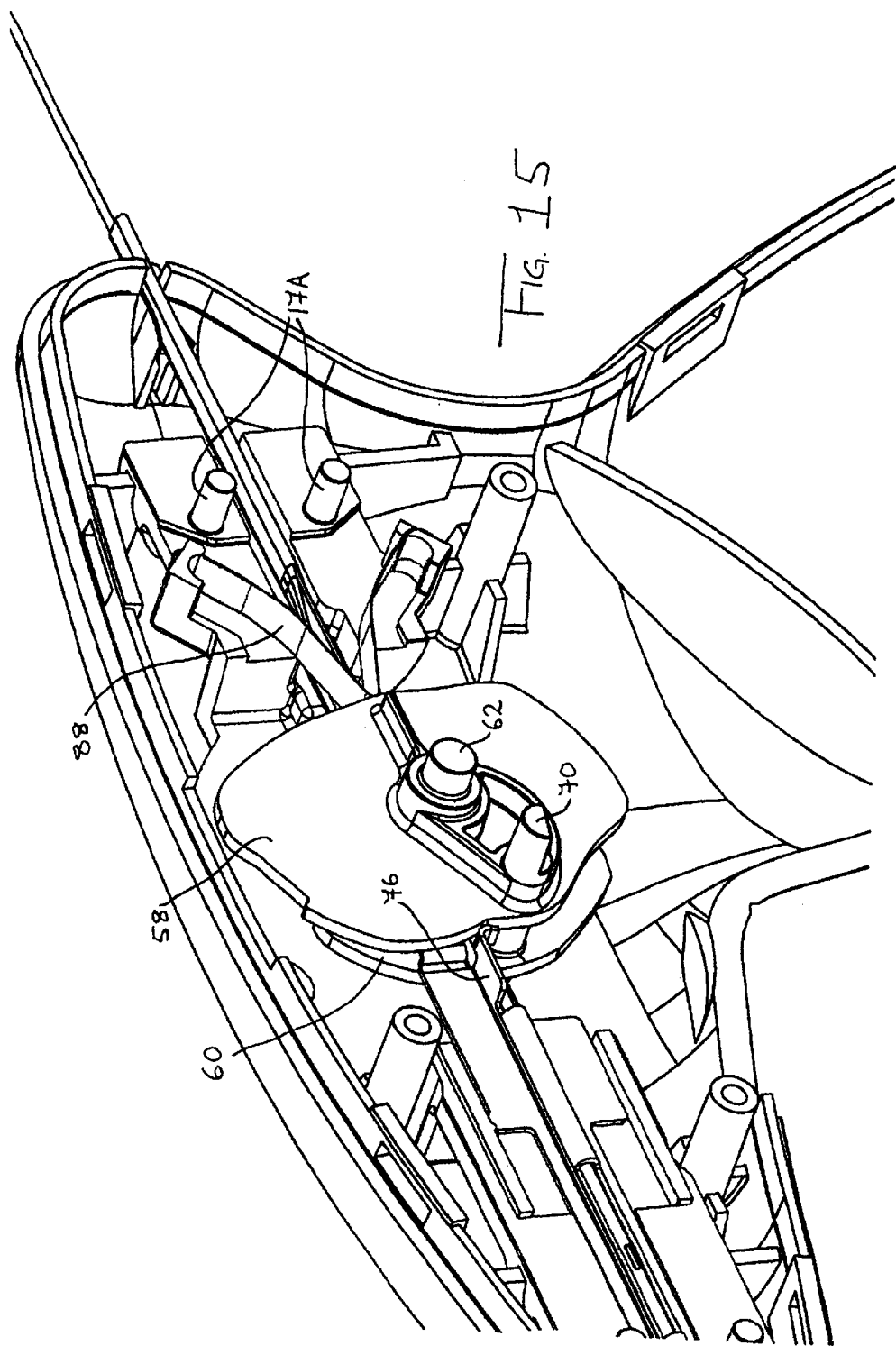

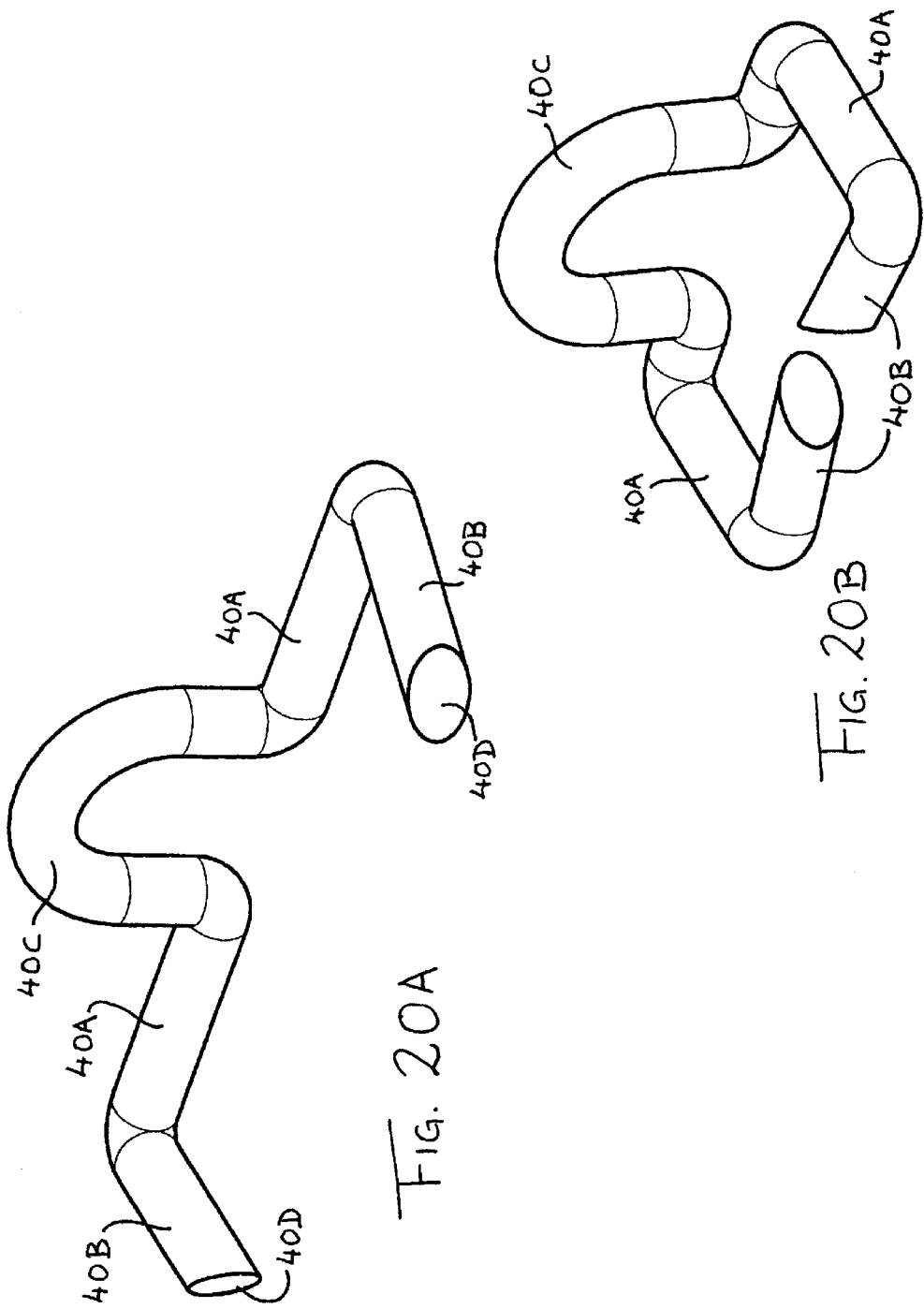

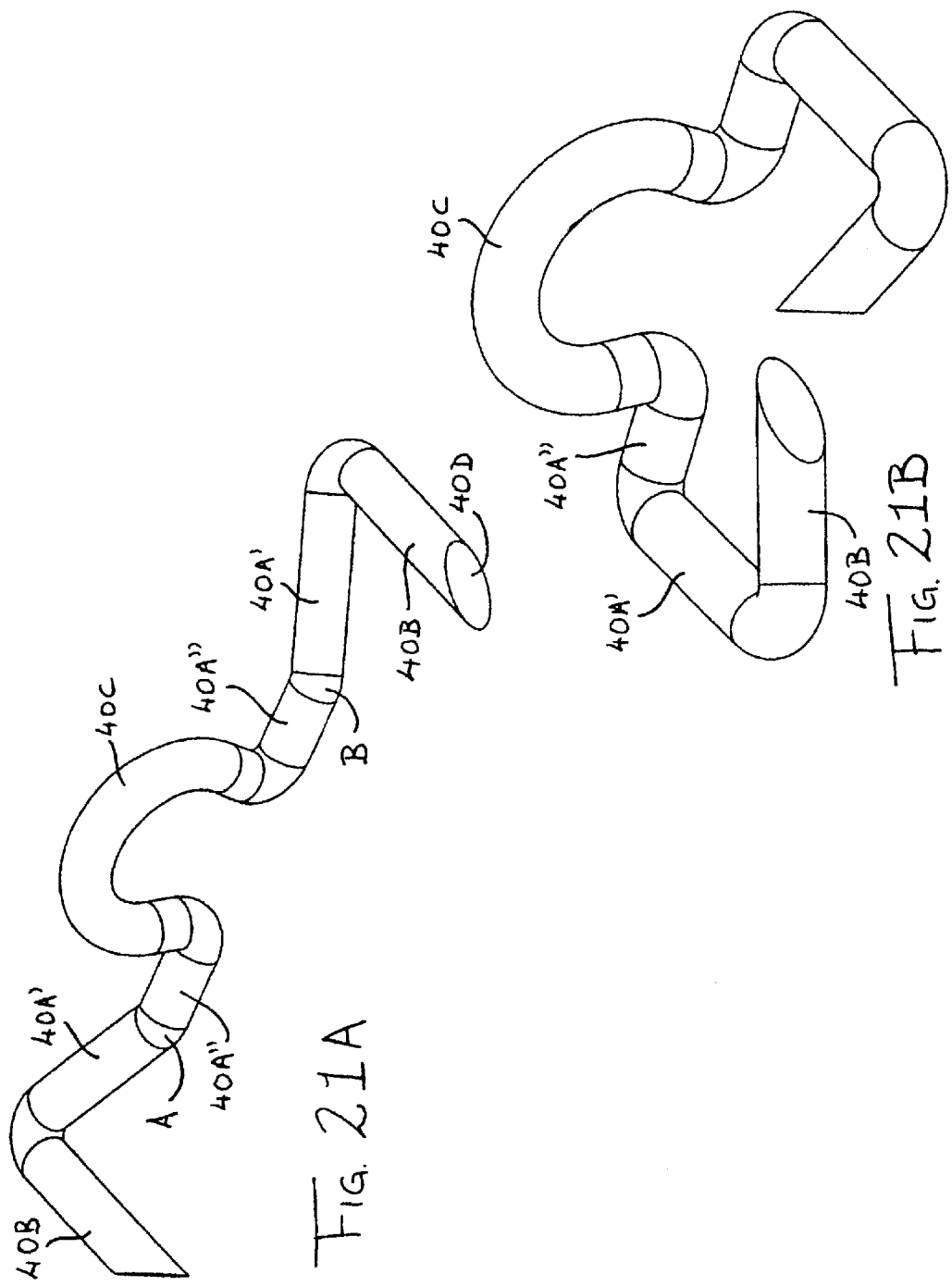

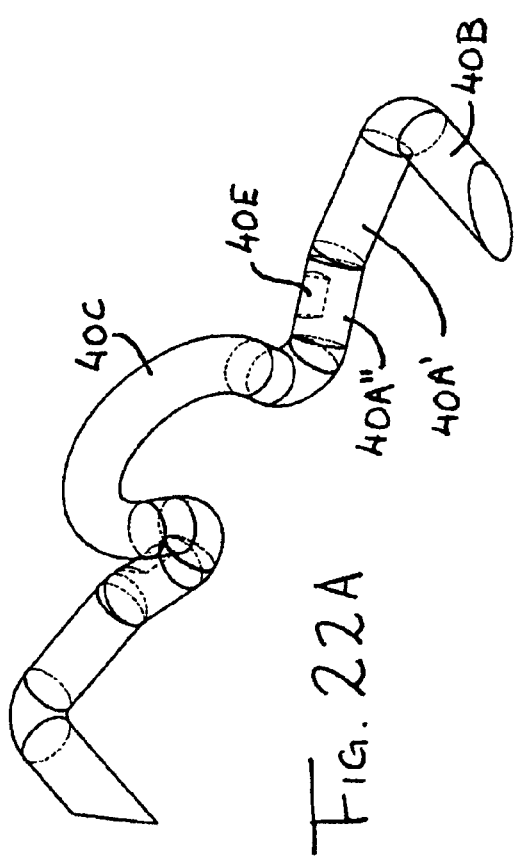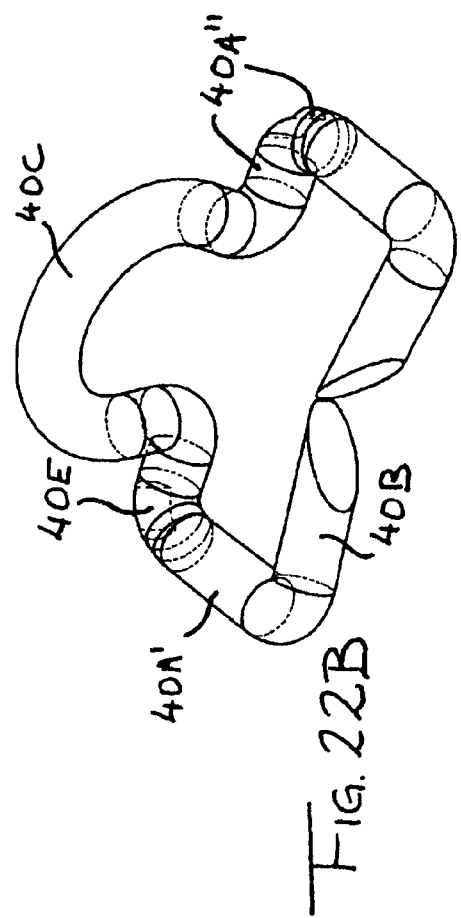

SURGICAL STAPLES AND METHODS FOR STAPLING

FIELD OF THE INVENTION

The present invention relates a surgical staple, for closing a puncture site in a liquid-carrying vessel in a human or animal body, for example a blood vessel, by applying a staple across the puncture so as to affect a closure and prevent bleeding. The invention also relates to a method of stapling using such a staple.

BACKGROUND OF THE INVENTION

When performing catheterisation procedures, such as angiography or angioplasty, a catheter is generally introduced into the vascular system by first penetrating the skin, underlying tissues and blood vessel with a sharpened hollow needle. Next, a guidewire is commonly inserted through the lumen of the hollow needle and is caused to enter the selected blood vessel. Subsequently the needle is typically stripped off the guidewire and a combination of a dilator and/or introducer (or an introducer alone) are fed over the guidewire and pushed through the skin to enter the blood vessel. The guidewire can then be removed and a desired catheter to carry out the procedure is fed through the lumen of the introducer and advanced through the vascular system until the working end of the catheter is appropriately positioned. Following the conclusion of the catheterisation procedure the working catheter will be withdrawn and subsequently the dilator and/or introducer will also be removed from the wound. Following this procedure the vessel puncture must be closed in order to prevent loss of blood through the puncture hole.

Typically the wound is closed by maintaining external pressure over the vessel until the puncture naturally seals. This procedure can take approximately 30 minutes with the length of time usually being greater if the patient is hypertensive or anticoagulated. The procedure can also be uncomfortable for the patient and involves costly professional time on the part of the hospital staff. Other pressure techniques such as pressure bandages, sandbags or clamps have been employed but these also involve ensuring the patient remains motionless for an extended period of time and is monitored to ensure the effectiveness of the procedure.

A number of devices have been developed in recent times which provide an obstruction in the area of the puncture in order to prevent bleeding. For example, U.S. Pat. Nos. 4,852,568 and 4,890,612 disclose a device which utilises a collagen plug which when placed at the blood vessel opening absorbs body fluids, swells and affects a seal. Other plug like devices, for example U.S. Pat. Nos. 5,222,974 and 5,282,827, describe a plug and anchor device, the anchor being positioned inside the vessel and the collagen plug outside the vessel thereby sandwiching the puncture between both and effecting a closure.

WO 98/17179 discloses a surgical stapler having a blood locator tube adjacent the stapling head. A guidewire passes through an opening at the end of the tube and up through a hollow bore in the tube, so that the stapler can be fed onto the guidewire and down onto the puncture site. When the device reaches the puncture site, the tip of the tube enters the blood flow within the artery and blood passes through the tube and out of the distal end at a point visible to the clinician. The clinician can then actuate the stapling mechanism in the knowledge that the stapling head is at the puncture site in the arterial wall.

It is an object of the present invention to provide an improved surgical staple for closing a puncture in a liquid-carrying vessel. It is a further object of the invention to provide an improved method of stapling using such a staple.

SUMMARY OF THE INVENTION

According to the present invention there is provided a surgical staple comprising a base portion and a respective leg extending from each end of the base portion and terminating at a free end, the base portion being deformable to bring the free ends of the legs together to penetrate a liquid-carrying vessel at the site of a puncture and hold the opposite edges of the puncture together, the base portion and legs lying in substantially a common plane except for a center portion of the base portion which is deformed in a loop at an angle to the common plane.

In another aspect the invention provides a method of stapling closed a puncture site in a liquid-carrying vessel in a human or animal body, comprising the steps of:

introducing a stapling mechanism to the location of the vessel;

positioning the stapling mechanism at the puncture site by means of an elongated locator device associated with the stapling mechanism, the locator device sensing the position of the puncture site by entering the vessel at the site; and delivering a staple to, and deforming the staple to close, the puncture site;

wherein the staple comprises a base portion and a respective leg extending from each end of the base portion and terminating at a free end, the base portion being deformable to bring the free ends of the legs together to penetrate a blood vessel at the site of a puncture and hold the opposite edges of the puncture together, the base portion and legs lying in substantially a common plane except for a center portion of the base portion which is deformed in a loop at an angle to the common plane; and wherein during delivery of the staple to the puncture site the staple loop straddles and slides along the locator device.

BRIEF DESCRIPTION OF THE DRAWINGS

Embodiments of the invention will now be described, by way of example, with reference to the accompanying drawings, in which:

FIG. 1(A) is an enlarged perspective view of the free end of the shaft of the stapler of FIG. 1;

FIG. 11A is an enlarged view of the front portion of the blood locator tube shown in FIG. 11;

FIG. 11B is an enlarged view of the rear portion of the blood locator tube shown in FIG. 11;

FIG. 13 is a perspective view of the front portion of the blood locator tube shown in FIG. 12;

FIG. 13(A) is a perspective view of the front portion of an alternative construction of the blood locator tube shown in FIG. 12;

FIG. 14(A) is a perspective view of the surgical staple in the pre-fire (pre-deformed) state;

FIG. 14(B) is a perspective view of the surgical staple in the post-fire (deformed) state;

FIG. 15 is an enlarged perspective view of the cam mechanism;

FIGS. 20(A) and (B) are pre- and post-fire views of a second embodiment of staple according to the invention;

FIGS. 21(A) and (B) are pre- and post-fire views of a third embodiment of staple according to the invention;

FIGS. 22(A) and (B) are pre- and post-fire views of a fourth embodiment of staple according to the invention;

DETAILED DESCRIPTION OF THE PREFERRED EMBODIMENTS

Figure 2:
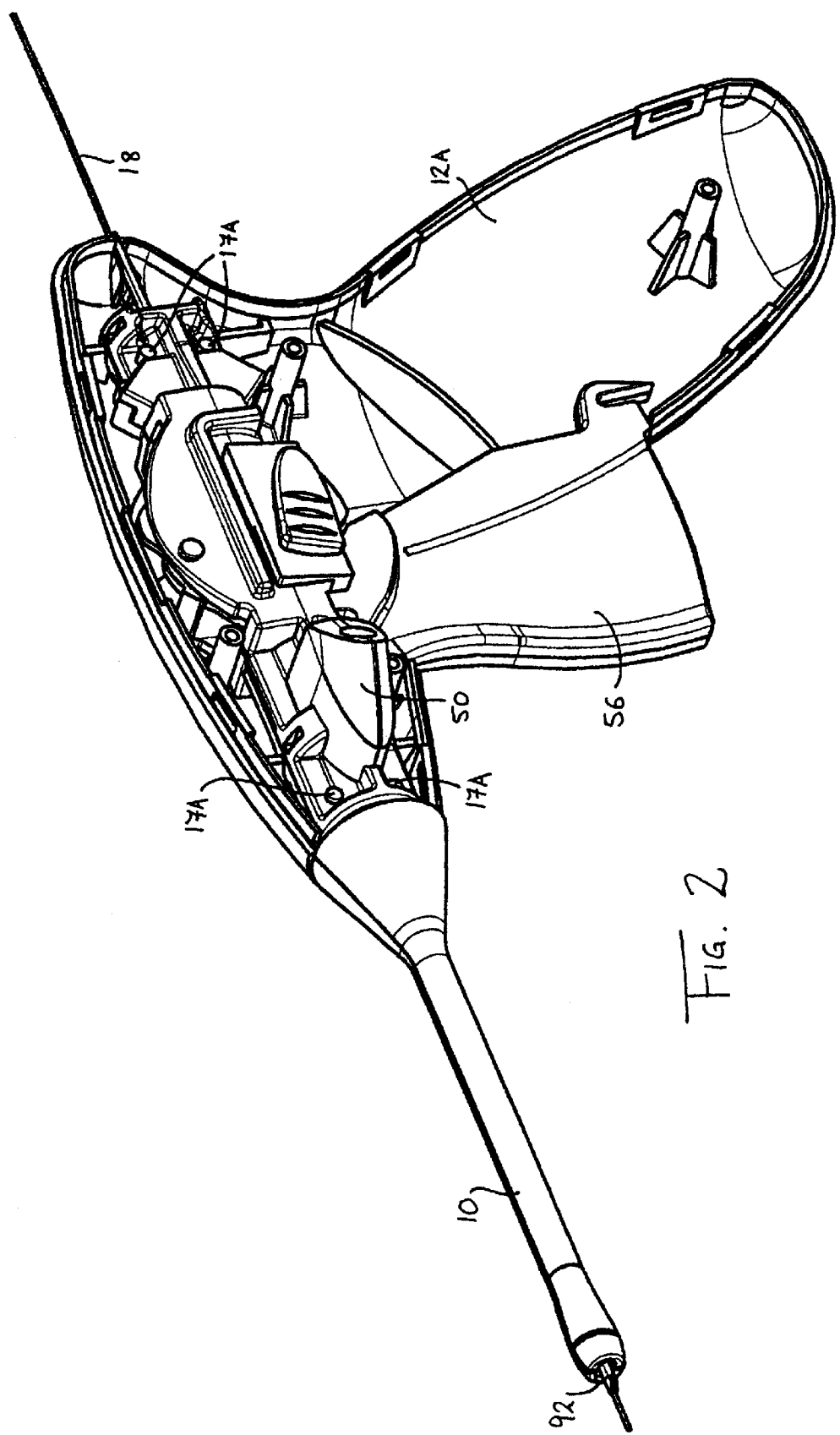
FIG. 2 is a perspective view of the stapler of FIG. 1 with the left-hand side handle removed.
Figure 4:
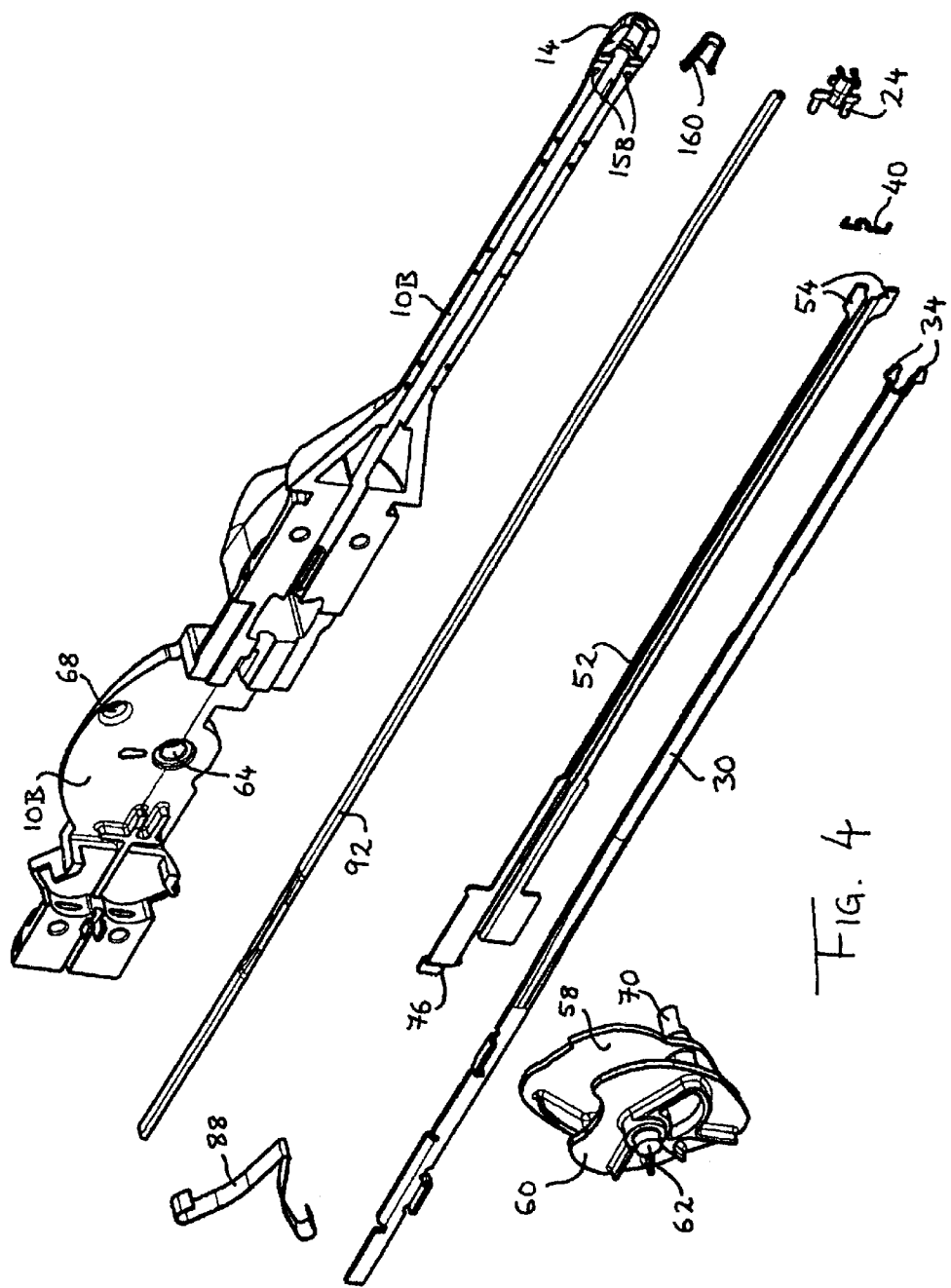
FIG. 4 is an exploded perspective view of the components seen in FIG. 3 further omitting the left-hand side handle.
Figure 5:
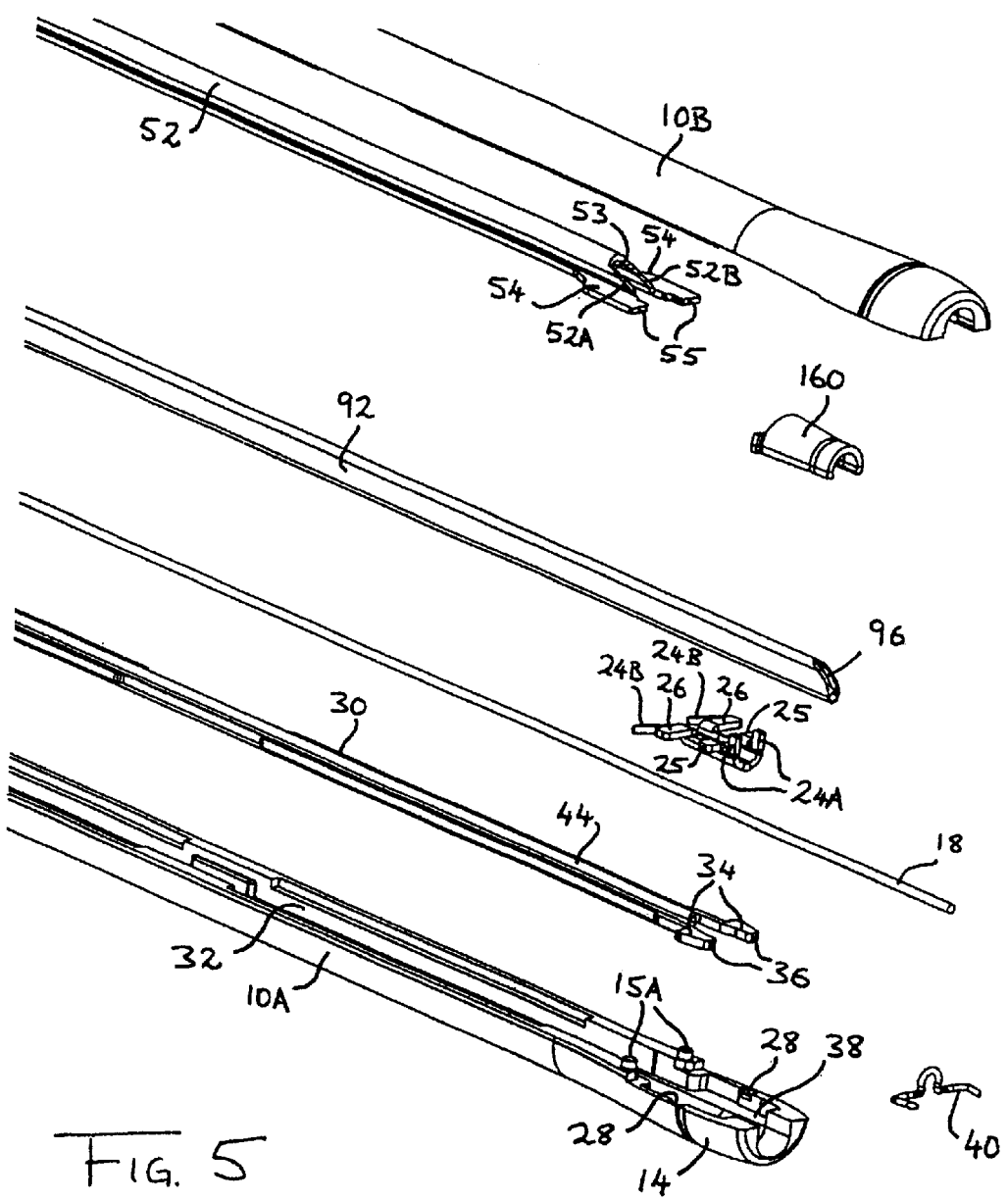
FIG. 5 is an exploded perspective view of the internal components at the free end of the shaft.

Referring to the drawings, the stapler comprises a rigid shaft 10 extending from a moulded plastic housing 12 shaped in the form of a pistol-like handle. The shaft 10, which is hollow to accommodate various moving components to be described, comprises right and left hand sides 10A, 10B respectively which are secured together at the distal free end by a section of heat shrinkable tubing 91 in combination with interference pins and mating cavities 15A and 15B (FIGS. 4 and 5) along the edges of the distal tip, and at the proximal end by pins 17A mating in an interference fit with corresponding cavities 17B (FIGS. 2 and 3) captured within the housing 12. Likewise, the housing 12 comprises left and right-hand sides 12A, 12B respectively.

The major part of the exposed length of the shaft 10 has a constant circular cross-section, but at its free end the shaft 10 has a portion 14 of increased diameter having a "bullet" profile. One end of this bullet portion 14 is tapered down toward a staple exit slot 16 while the other end is tapered down to the remaining section of the shaft, which extends back into the housing 12. The ratio of the maximum diameter of the bullet portion 14 to the diameter of the remaining section of exposed shaft is approximately 5:4. Heat shrink sleeve 91 sits flush with the surface of the bullet portion 14, to ensure atraumatic entry, percutaneously, into the tissue.

The reason for the bullet profile is so that the shaft 10 is as atraumatic as possible during introduction to the body to minimise the amount of force and tissue dilation required when tracking the device percutaneously over a guidewire 18 and onto the surface of a blood vessel adjacent a puncture hole, as will be described. In an alternative construction, not shown, the bullet portion 14 is oval in cross-section with the major axis of the oval being coincident with the staple exit slot 16, so as to minimise the circumferential length for a given staple width.

The bullet portion 14 of the shaft 10 houses a staple 40 and a staple delivery mechanism (FIGS. 4 to 7). The staple delivery mechanism comprises a tiltable anvil 24 and a pair of rod-like actuating members, namely an elongated anvil support 30 and an elongated staple former 52, the latter being slidable in the shaft 10 and operated by a trigger-operated cam mechanism 62 in the handle housing 12.

The anvil 24 has a pair of upstanding fingers 24A at the front and a pair of downwardly inclined tilt arms 24B at the rear. The anvil 24 is tiltably mounted in the bullet portion 14 by a pair of wings 26 which are pivotable in recesses 28 in the right hand side 10A of the shaft 10 (the wings 26 are retained in the recesses by the underside of projections 54 on the former 52).

Figure 6:
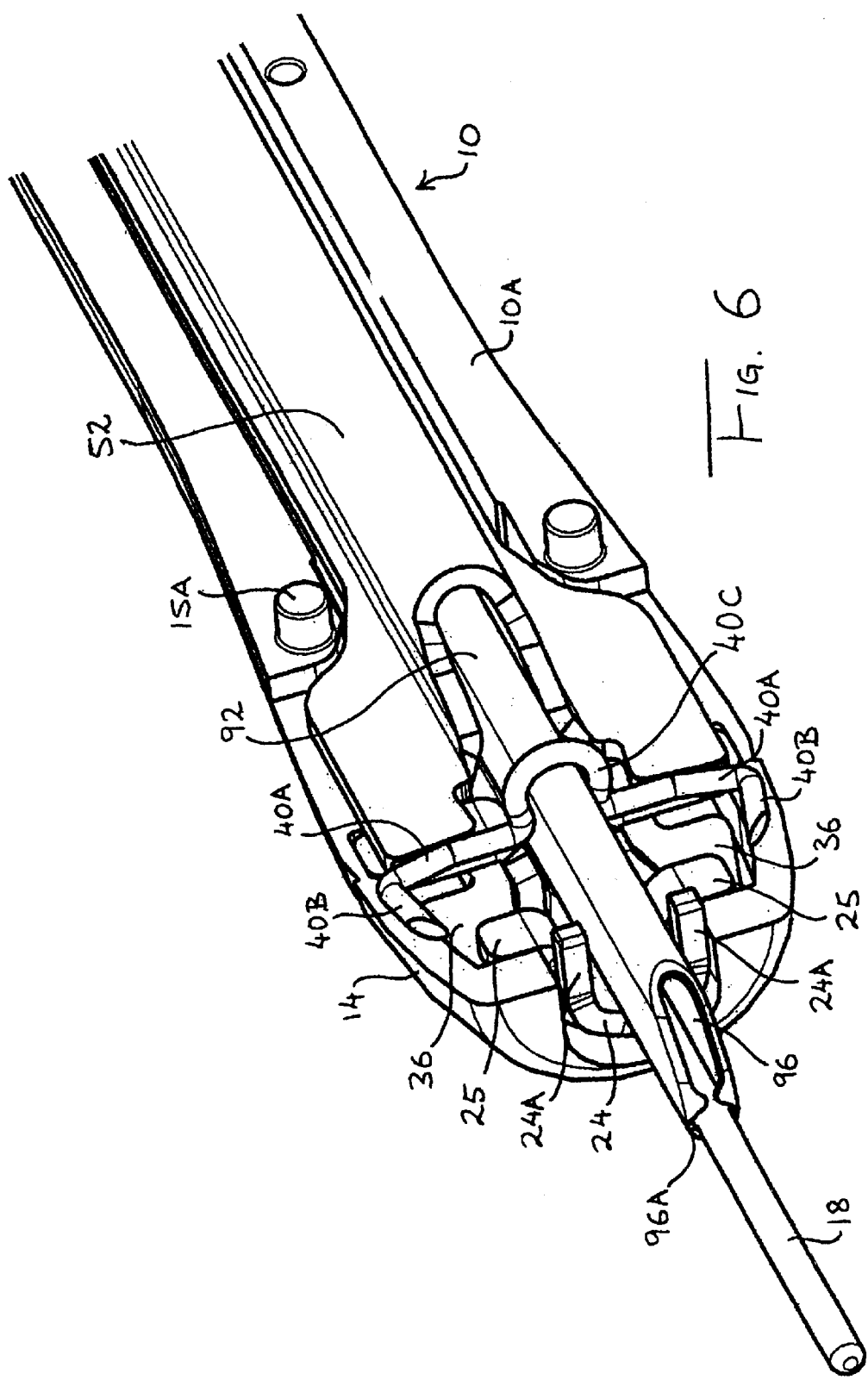
FIG. 6 is a perspective view of the internal components at the free end of the shaft in the pre-fire position and omitting the left hand side of the shaft.
Figure 7:
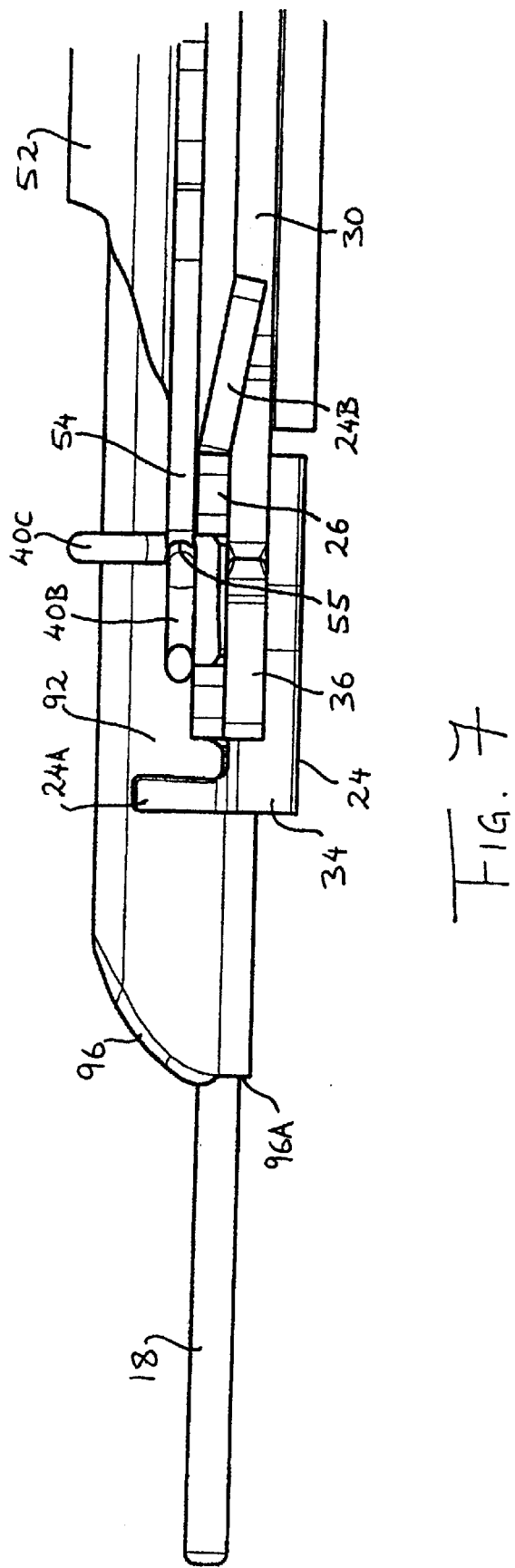
FIG. 7 is a side elevation of the components of FIG. 6 in the pre-fire position.

Tilting of the anvil 24 is effected by the cam mechanism 62 via the anvil support 30, which is slidable axially within the right hand shaft side 10A in channel 32. The front end of the anvil support 30 is bifurcated to form two arms 34 having lateral projections 36 (FIGS. 6 and 7). The arms slide in rebates 38 in the right hand shaft side 10A. The anvil support 30 is movable, by the cam mechanism 62, from a forward position, FIGS. 6 and 7, wherein the arms 34 extend under the anvil's support wings 25 to support the anvil forming fingers 24A directly in front of a surgical staple 40 to be delivered, to a rearward position, FIG. 10, wherein the arms 34 are withdrawn under the downwardly inclined tilt arms 24B at the rear of the anvil 24 so as to tilt the anvil anti-clockwise (as seen in FIG. 10) and displace the fingers 24A out of the path of the staple 40.

Figure 11:
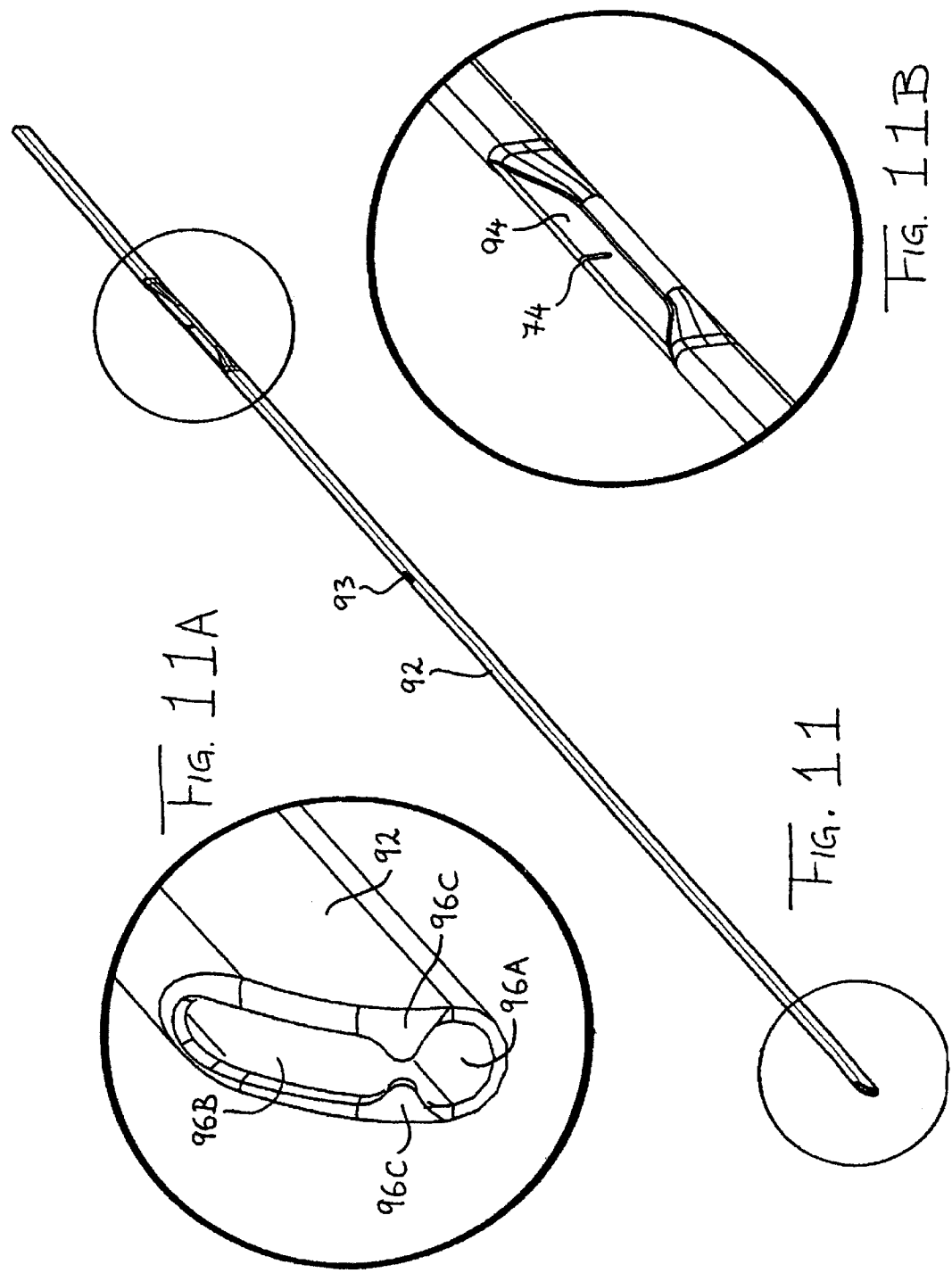
FIG. 11 is a perspective view of the blood locator tube.

Referring additionally to FIGS. 11, 11A and 11B, a hollow blood locator tube 92 is slidable axially within the shaft 10 in a channel 44 in the anvil support 30 and in an opposing U-shaped channel 53 in the staple former 52. The tube 92 extends the full length of the shaft 10 and has a constant, generally oval or elongated cross-section, except at its distal tip 14 where the locator tube 92 is formed into a narrow opening 96 and at a crimped region 94 towards the rear of the tube 92 which is formed to allow only the guidewire 18 and not blood to exit the rear of the locator tube.

Figure 9:
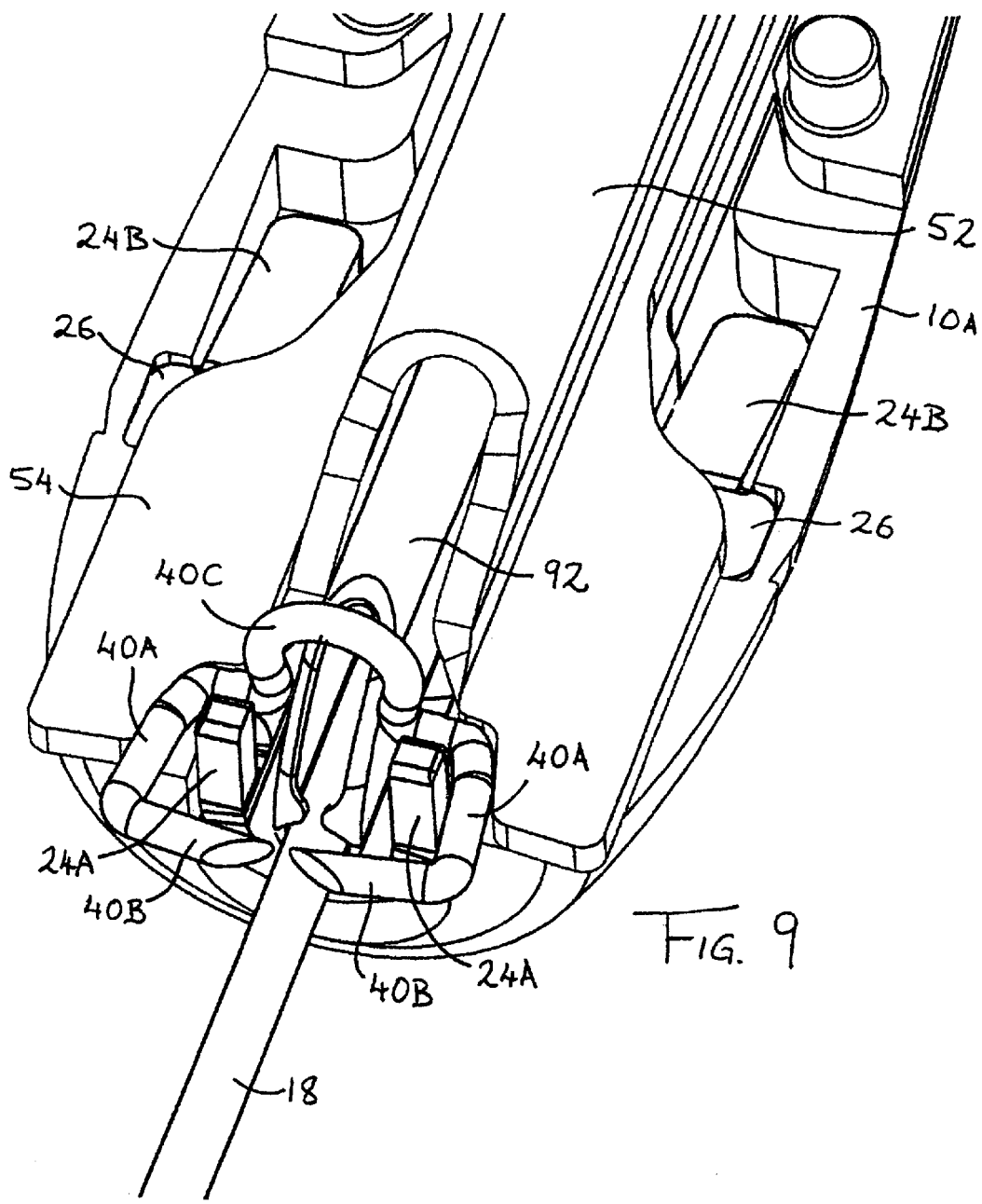
FIG. 9 is a perspective view of the internal components of the free end, showing the position of the components in mid-cycle with fully formed staple.
Figure 10:
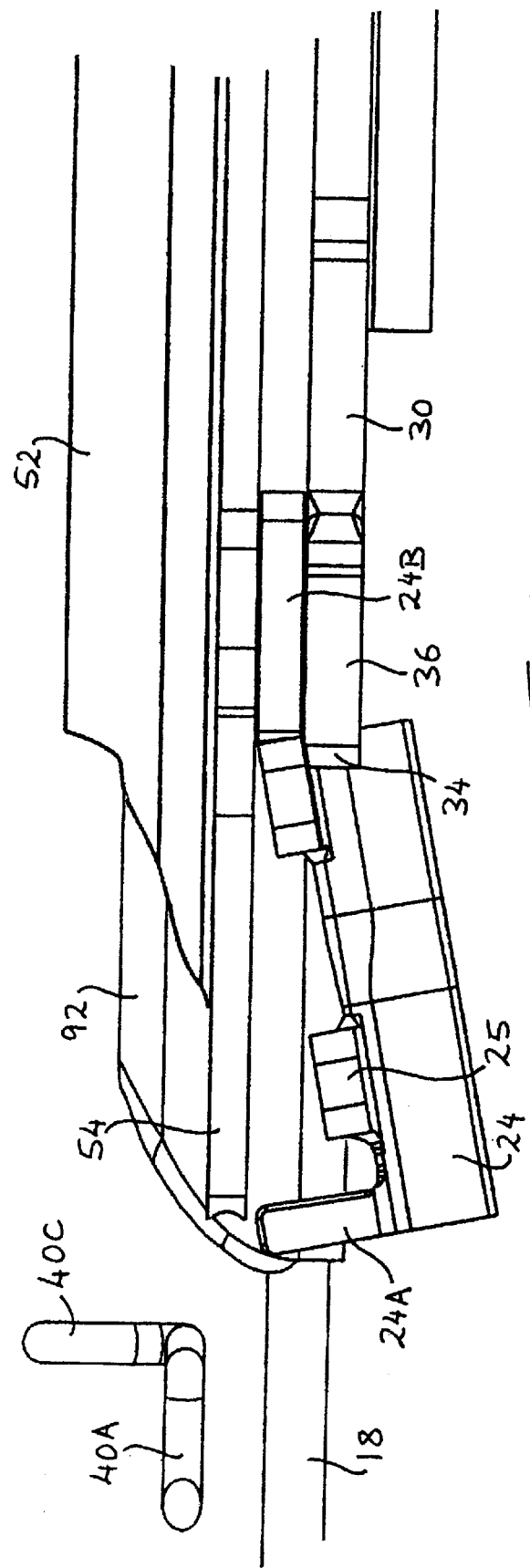
FIG. 10 is a side elevation of the components of FIG. 9 in the post-fire position.

Under the action of the cam mechanism 62 the tube 92 is slidable axially in the shaft 10 between a forward position, FIGS. 6 and 7, wherein its front end projects beyond the bullet portion 14 of the shaft 10 under the influence of a leaf spring 88 to be described, and a rearward position, FIGS. 9 and 10, wherein the front end of the tube 92 is retracted within the bullet portion 14 behind the fingers 24A of the anvil 24 during the rotation of cam 62.

Figure 1:
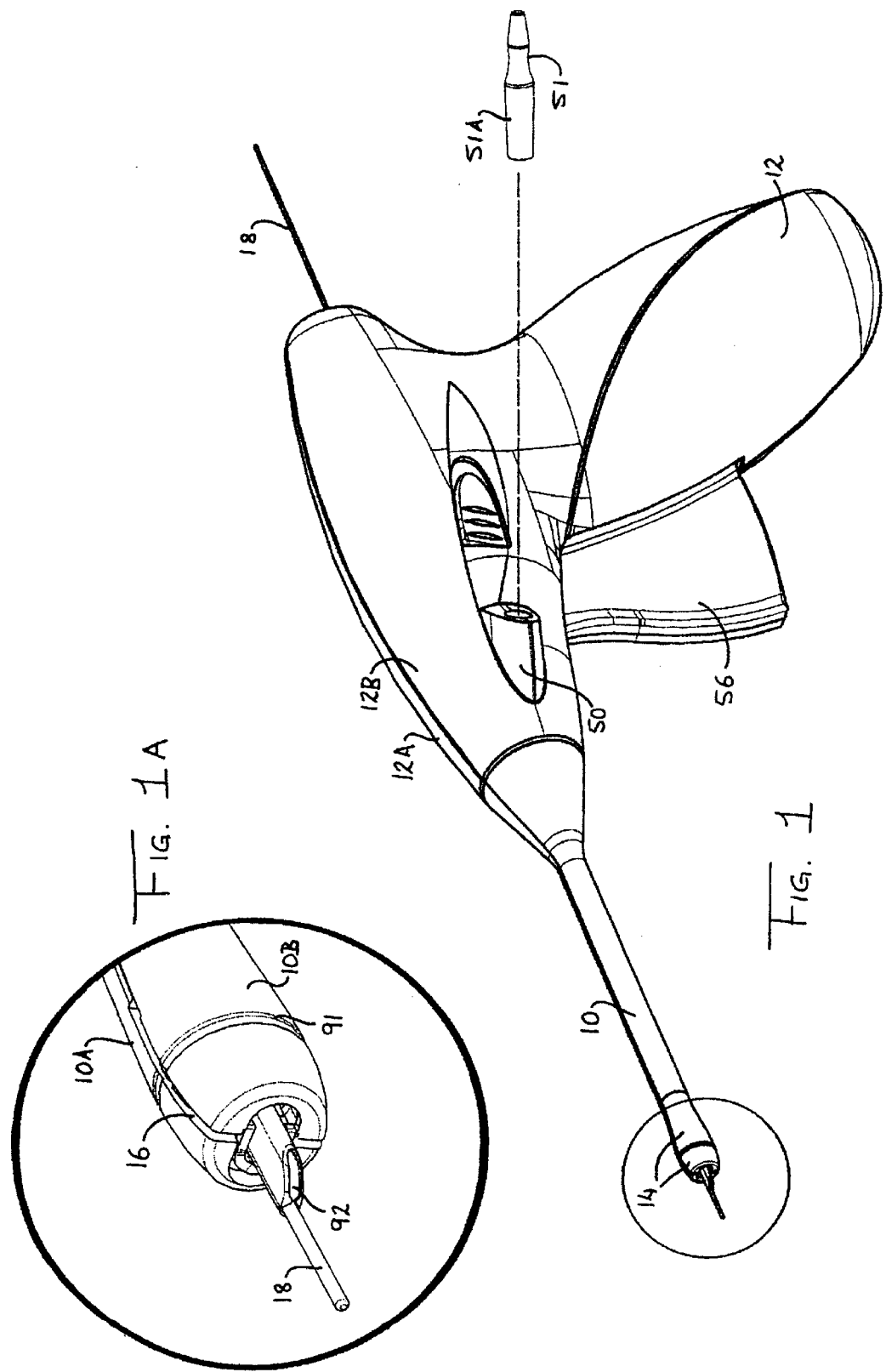
FIG. 1 is a perspective view of a surgical stapler incorporating a staple according to the invention.

The purpose of the blood locator tube 92 is to follow a previously placed guidewire 18 to a puncture site in a blood vessel, thereby to locate the free end of bullet portion 14 of the shaft 10 against the exterior wall of the blood vessel at the puncture site. To properly locate the bullet portion 14 the front end of the tube 92 must actually penetrate the blood vessel wall at the puncture site and this is indicated by blood flowing back through the tube 92 and out through a blood outlet port 93 (FIG. 11) in the tube. A channel (not shown) in the part of the left hand side 10B of the shaft 10 within the housing 12 provides communication between the port 93 and a blood exit port 50 (FIG. 1) on the side of the housing 12B, so that the blood flowing back through the tube 92 is visible at the exterior of the housing.

A blood exit port adapter 51 (FIG. 1) may be secured into the opening of the blood exit port 50 via a matching male luer taper 51A to enhance the visibility of the exiting blood. The blood exit port adapter has a reduced internal diameter, relative to the opening of the blood exit port 50, which for a constant blood flow increases the pressure of exiting blood causing a jet effect of exiting blood.

In the absence of the blood exit port adapter, the blood exit port's female luer taper opening matches that of the standard medical syringe's male luer taper making it possible at any time during the device's use to inject fluid via the blood exit port into the lumen of the locator tube to exit at its distal tip. This may be necessary from time to time to clear the locator tube's lumen of congealed blood or trapped soft tissue. Alternatively, radiopaque contrast medium may be injected via the locator tube to confirm the relative location of the locator tube's distal tip to that of the blood vessel wall by fluoroscopy, or any injectable fluids may be injected for diagnostic or therapeutic reasons.

The blood outlet port 93 is sized to have a minimum area corresponding to the available blood entry area at the distal tip; however, is narrower (in a transverse aspect) than the diameter of the guidewire 18 to prevent the guidewire inadvertently exiting the blood outlet port during insertion, instead of exiting from the intended proximal end of the locator tube.

It has been found that the naturally formed shape of puncture wounds in arterial walls is elongated rather than round. Whereas the hole is formed by introducing instruments generally of round cross section, the wall tends to open generally along a transverse line which lies in the direction of the circumference of the artery (rather than along the axis of the artery). By having a generally oval blood locator tube, the locator tube (when introduced by the clinician with the major axis of the oval perpendicular to the axis of the artery), will fit more naturally within the arterial opening. The consequence of this is that the wound edges which are to be stapled together, lie closer together than if a tube of circular cross section were to be used.

This in turn has the consequence that the staple used need not be so large, and in turn, the dimensions of the shaft, which must accommodate the staple when in its unformed state, can be reduced, leading to less trauma for the tissue into and from which the shaft is introduced.

A further consequence of having a generally oval or elongated cross section for the locator tube is that the tube will be more disposed to the center of the puncture than with a rounded tube. The present embodiment has a staple which straddles the locator tube, thereby increasing the likelihood of the staple closing the elongated wound at its center rather than towards one or other of the extremities of the wound.

The opening 96 at the front of the tube 92 has an approximately circular portion 96A at the extreme forward tip of the tube which is of greater diameter than the width of the remaining portion 96B of the opening 96. The portion 96B is in the form of a slot which is aligned with the major axis of the elongated cross-section of the tube 92 and slopes rearwardly from the circular portion 96A. The guidewire 18, which passes through the tube 92, FIG. 11, is chosen to be of sufficiently smaller diameter than the diameter of the opening 96A at the front end of the tube 92 for the guidewire 18 to be easily inserted into the tube 92 and pass through the opening 96A. However, the guidewire is also chosen to be too large to fit within the remainder 96B of the opening 96. In this way guidewire 18 is constrained to remain in opening 96A, and the size of opening 96A sets an upper limit on the diameter of guidewire which can be used with the device. One could introduce a narrow neck or constriction into the opening 96 just above opening 96A (at the points indicated by 96C) to ensure that very small guidewires were constrained within the enlarged opening 96A, but in general this is unnecessary as the guidewire will normally be supplied with the device, or the device will only be supplied for use with a particular gauge of guidewire.

The rear crimp 94 and tip opening 96A are positioned to encourage the guidewire to lie along the bottom curved surface of the tube, i.e. that portion of the tube lying in a direct line between the opening in the crimped end and the opening 96A. This helps prevent guidewire 18 from laying up against the inside of blood exit port 93 and preventing egress of blood, FIGS. 11A and 11B.

The curvilinear nature of opening 96 increases the available inlet area to match that of the available area within the body of the locator tube with the guidewire 18 in situ.

The slot-like opening 96B slopes away from the circular opening 96A for ease of insertion into the vessel opening and to reduce the potential of trauma to the inner wall of the vessel opposite the opening being stapled. This is achieved because the guidewire 18 protruding from opening 96A will tend to push the opposite wall of the vessel away from the locator tube tip, and the point at which the guidewire protrudes (due to it being constrained in the opening 96A) is the farthest part forward of the tip. Thus, the shape of the tip is streamlined away from opening 96A to prevent any part of the tip gouging into or otherwise damaging the inner vessel walls. Also, the peripheral edges 95 of the opening 96 are bent inwardly to as to avoid sharp edges which might damage soft tissue and the vessel wall.

Figure 12:
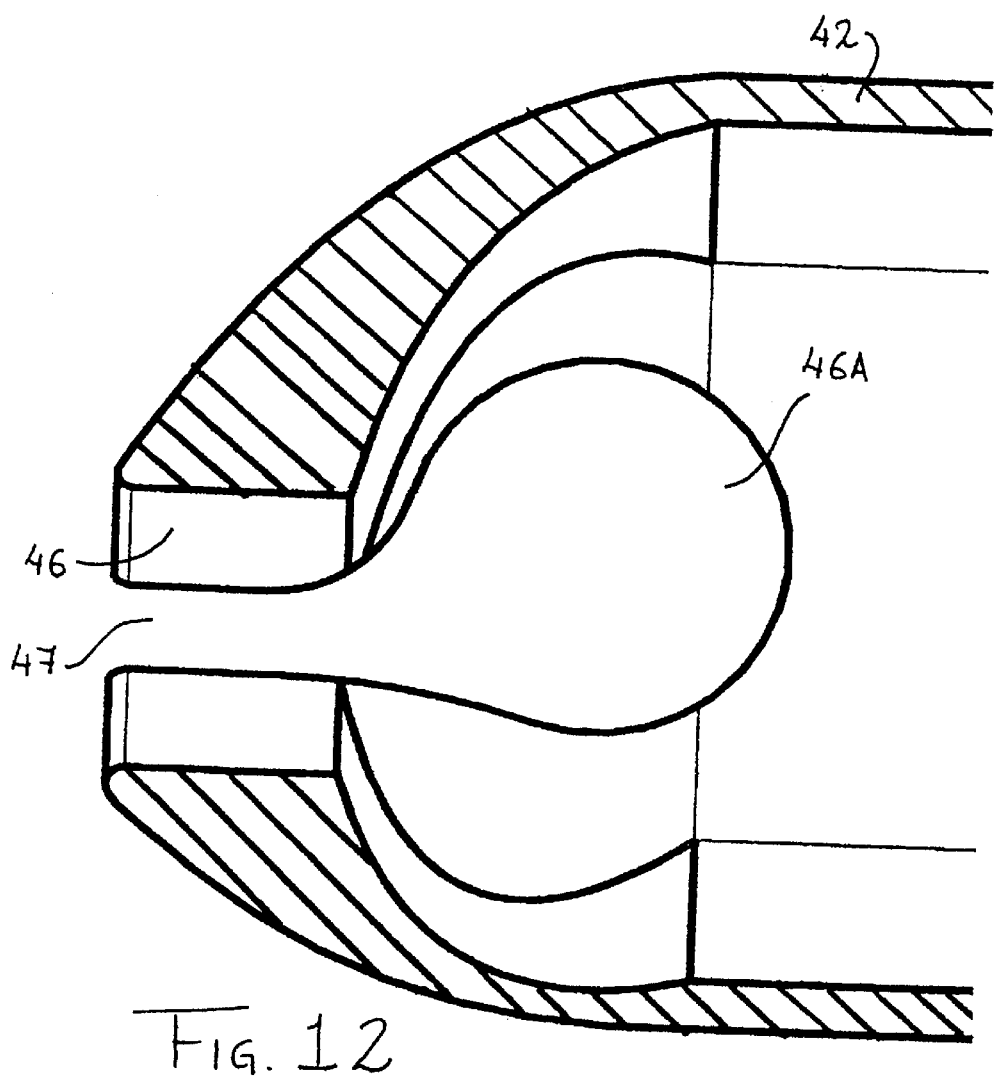
FIG. 12 is a side sectional elevation of the front portion of an alternative construction of the blood locator tube of the stapler.

The distal end of an alternative construction of a locator tube 42 is shown in FIGS. 12 and 13. This construction also has a substantially constant elongated cross-section, which in this case converges to an approximately circular guidewire opening 46 at the extreme forward tip of the tube. The guidewire 18, which passes through the tube 42, is usually chosen to be of sufficiently smaller diameter than the diameter of the opening 46 for there to be an adequate gap for the blood to pass back through the tube 42 even in the presence of the guidewire. However, further openings 46A are provided in opposite sides of the tube 42 just behind the front opening 46 to allow more ready access of the blood to the interior of the tube in cases where the guidewire 18 may not leave a large enough gap for passage of blood solely through the opening 46. The three openings 46, 46A, 46A in fact form respective portions of a single front opening, being in reality three connected lobes, all connected by constricted channels 47, and all in communication with the interior of the tube.

An alternative construction is shown in FIG. 13(A) where the three openings 46, 46A and 46A, while collectively constituting the front opening of the tube 42, are independent of each other. Again, opening 46 at the front of the tube is sized to receive a maximum size of guidewire and openings 46A are sized to allow a sufficient flow of blood to enter the locator tube.

A problem can arise in devices of this type where an oversized guidewire is used which occludes the hollow interior of the blood locator tube and thereby prevents blood flow back through the tube. To prevent this situation the lobe 46 through which the guidewire emerges in the tip of the tube of FIGS. 12, 13 and 13A is of a lesser diameter than the internal bore of the tube. The dimensions of this lobe 46 set a maximum for the guidewire diameter for use with the device, and ensure that even when this maximum diameter guidewire is used, there is still sufficient internal clearance within the tube bore to allow a strong blood flow through the tube from the other lobes 46A.

Figure 8:
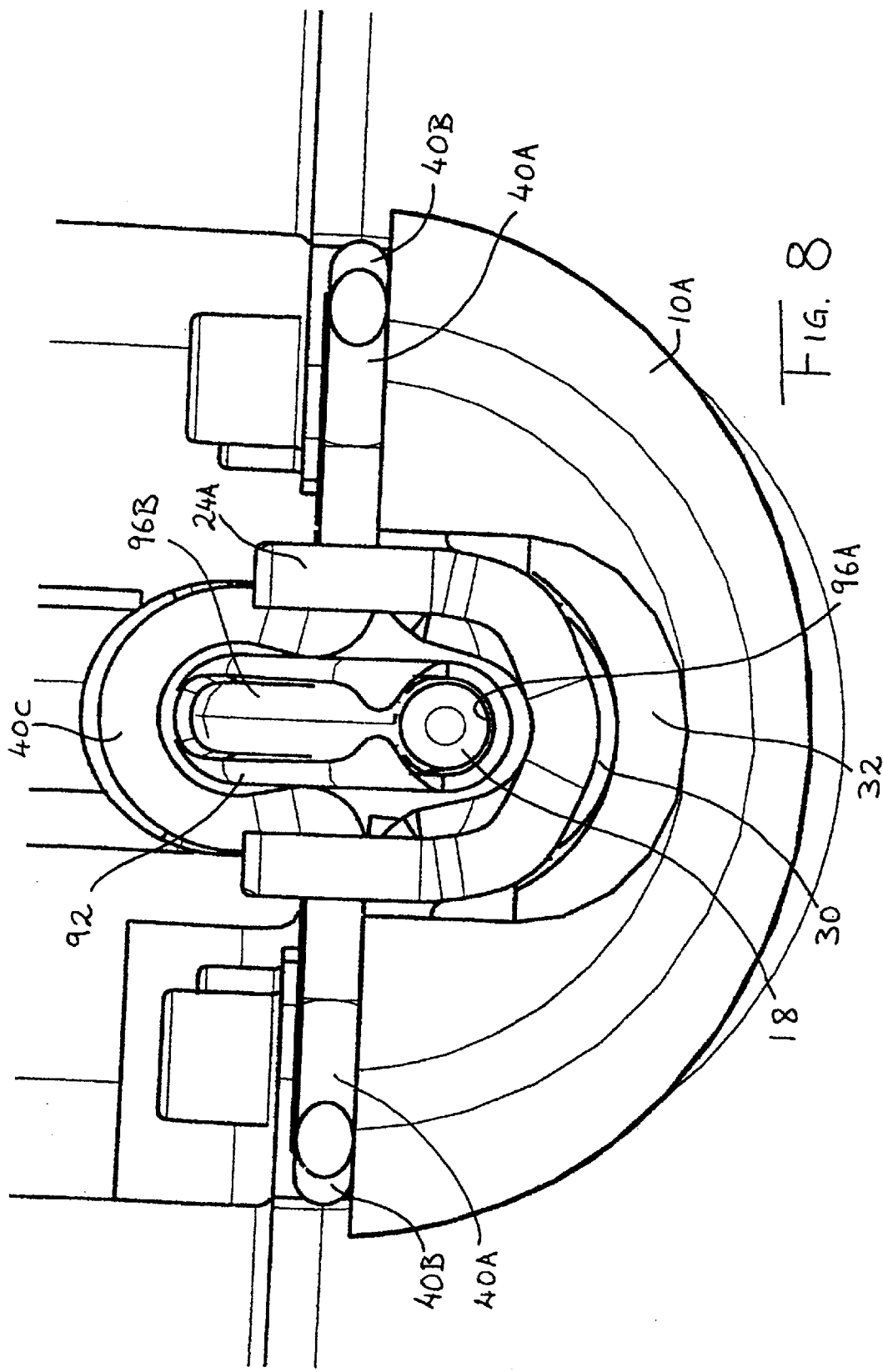
FIG. 8 is a front elevation of the components of FIG. 6 in the pre-fire position.

The staple 40 straddles the blood locator tube 92 within the bullet portion 14 of the shaft 10, see FIGS. 6 and 8, and is slidable thereon forwardly towards the free end of the bullet portion 14. In particular (see also the enlarged view of FIG. 14), the staple 40 comprises a back or base portion 40A from which extend approximately perpendicularly at each end respective legs 40B which terminate in sharpened points 40D. The legs 40B preferably converge at a small angle of, for example, about 10°–15°.

The base portion 40A and legs 40B lie in substantially a common plane except for a center portion of the base portion 40A which is deformed in a direction perpendicular to the legs 40B so as to have an Ω (omega) shaped loop 40C generally complementary to the external cross-sectional profile of the blood locator tube 92 and internal cross-section of an insert 160 to be described.

Figure 19A:
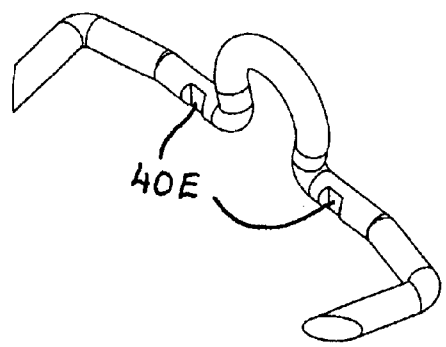
FIG. 19(A) is a perspective view of the staple of FIG. 14 showing an alternative location for bruise points.
Figure 19B:
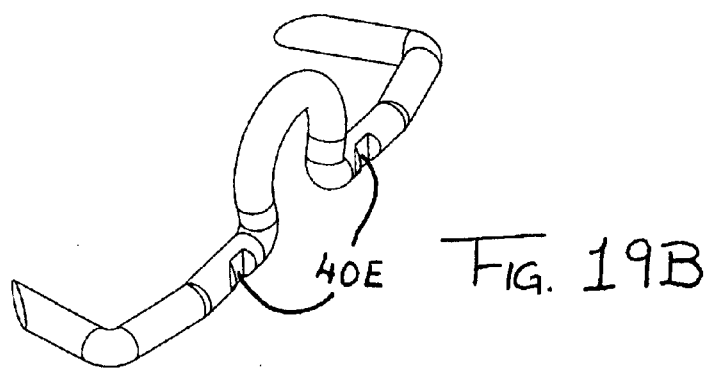
FIG. 19(B) is a perspective views of the staple of FIG. 14 showing an alternative location for bruise points.
Figure 19C:
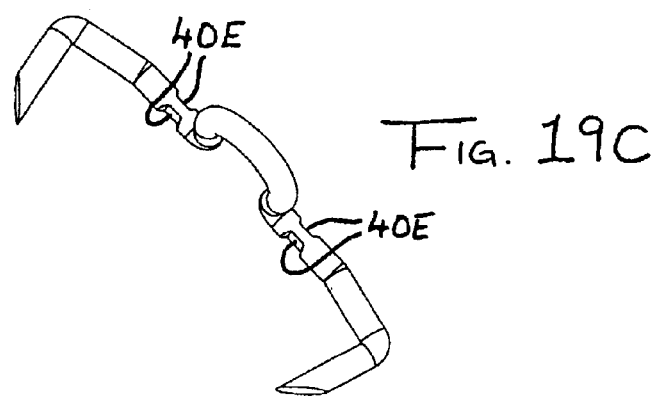
FIG. 19(C) is a perspective view of the staple of FIG. 14 showing an alternative location for bruise points.

At points A and B on each side of the omega section 40C, and at an equal distance therefrom, the outer ends 40A' of the base section 40A are pre-bent forwardly to make an angle of between 150° and 170° with the inner ends 40A" which lie substantially on a straight line, the pre-bend points A and B being positioned to maximise the closure of the closed staple (and is relevant to the depth of forming wings 54 on the former 52). The base section is also locally deformed ("bruised") at points 40E so as to narrow the cross sectional width of the wire at both points thereby directing the staple to bend at these points. As seen in FIG. 19, the bruise points 40E may be provided on the front of the base section (FIG. 19A), on the rear of the base section (FIG. 19B), or on both the front and rear of the base section (FIG. 19C).

Figure 24:
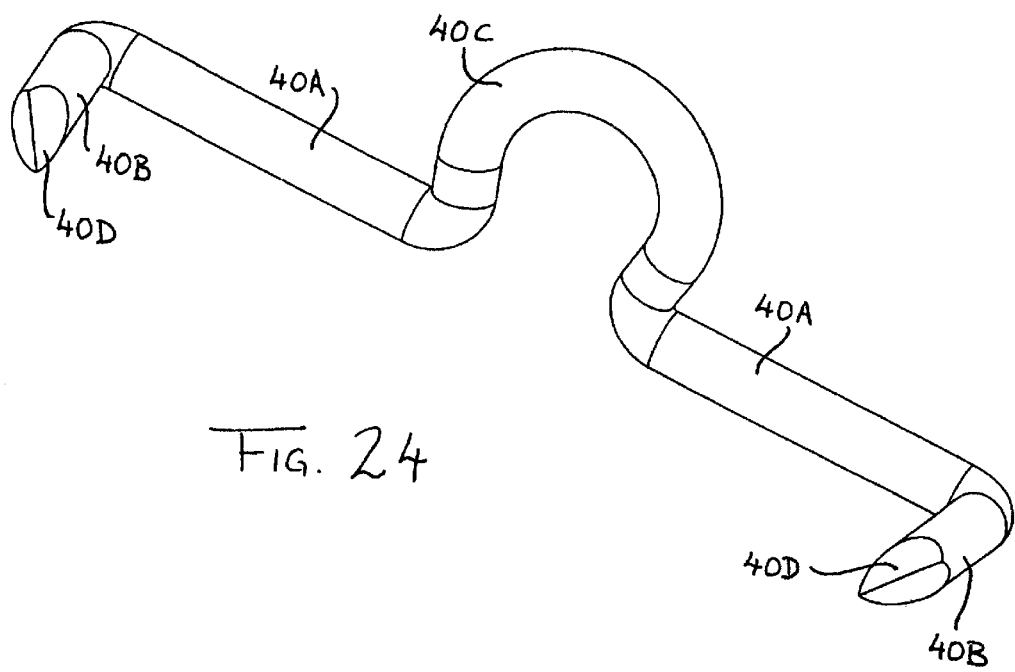
FIG. 24 is a pre-view of a sixth embodiment of staple according to the invention.

The tips of the points 40D are directed inwardly, i.e. in the direction in which the legs 40B are closed in use, as shown in FIG. 14B. Alternatively, the point geometry may involve two bevel planes so as to create a sharper pointed end (FIG. 24). The point geometry, angles of projecting legs 40B to base 40A and the length of legs 40B are configured to aid in keeping the closing staple within the thickness of the arterial wall and prevent the staple-points 40D penetrating into the arterial lumen, and additionally to avoid snagging on or dislodging any atheromatous or calcified plaque between the intimal and endothelial layers of the arterial wall.

The staple 40 is mounted on the blood locator tube 92 such that the center portion 40C of the staple sits on the upper half of the tube 92, as seen in FIGS. 6 and 8, where the narrow open section of the omega shape is approximately equal to the width of the tube and with the legs 40B pointing forwardly on opposite sides of the tube 92. The depth of the center portion 40C of the staple 40 is such that the legs 40B of the staple lie substantially directly on opposite sides of the central axis of the tube 92. This will ensure that the staple 40 is positioned centrally across the puncture hole in the blood vessel. In order to avoid the guidewire 18 fouling the staple 40 when the latter is closed on the puncture site, the hole 96A is offset below the plane containing the legs 40B of the staple, FIG. 8.

Figure 18:
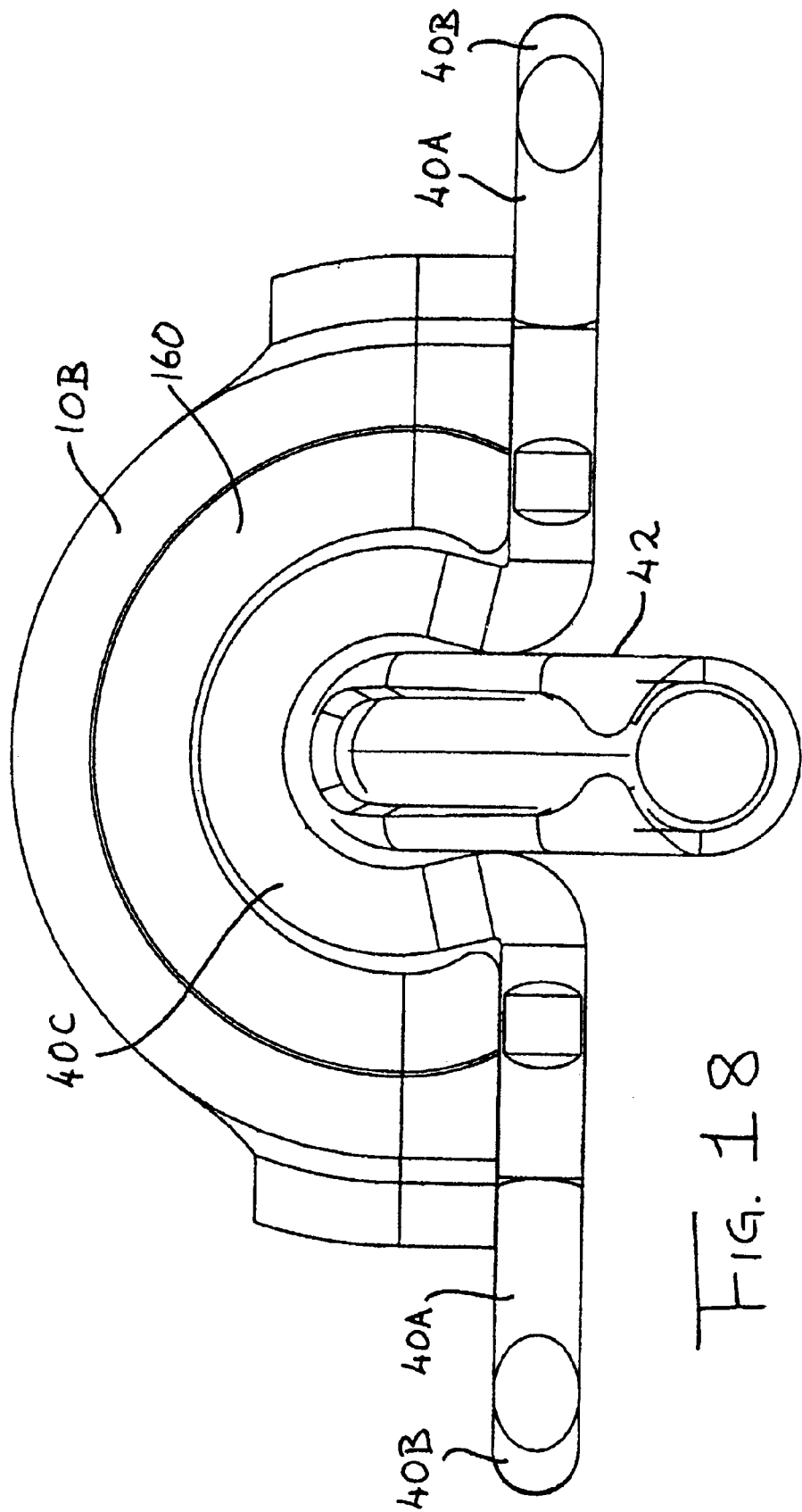
FIG. 18 is an end view of the surgical staple, locator tube and insert.

The metal insert 160 is received in a recess in the left-hand shaft side 10B within the bullet section 14. The insert 160 provides mechanical support for the omega section 40C of the staple 40 during the staple forming process and is engaged by the former 52 during the staple ejection phase of the process so as to separate both halves of the bullet section for easy staple release. The insert is profiled to generally correspond with the external profile of the omega shaped portion 40C of the staple. At the distal end the insert profile tapers down to closely approximate the omega-shaped portion of the staple 40C (FIG. 18) This has the effect of offering mechanical support to the omega-shaped portion of the staple during the staple forming process, during which the base section is bent about the anvil fingers 24A at the bruise points 40E. This bending motion in turn causes the omega to open up or flatten out. The metal insert prevents this from happening, only allowing the staple base to deform around the anvil at the bruise points 40E. The omega interlock system between the staple 40 and insert 160 (FIG. 18) also stabilises the staple, vertically, within the staple exit plain during the forming process, whilst allowing easy staple release once formed, due to the relatively small contact area between staple and insert.

The staple former 52 has a cross-section conforming to that of the blood locator tube 92 and is slidable on the blood locator tube 92 axially within the shaft 10. The former 52 is located behind the staple 40 on the tube 92 and is operated by the cam mechanism 62. At its front end the former 52 has a pair of forming arms 54 which are so shaped that, when the former 52 is driven forward by the cam mechanism 62, the staple 40 is driven against and deformed around the anvil fingers 24A so that the legs 40B of the staple close together (FIG. 9) onto the puncture site. The surface of the forming arms which contact the staple 55 may be so profiled to match the cross-sectional geometry of the staple. This matching profile stabilises the staple on the forming surfaces of the forming arms 54 during the high pressure contact with the staple during staple forming and closure. During the forward movement of the staple, the staple legs slide toward the anvil 24 along a track defined by the staple exit slot 16 between the opposite halves the bullet portion 14. The slot 16 provides a slight interference fit on the staple legs 40B to prevent the staple 40 moving forward during storage of the device or prior to firing. The slot 16 further prevents the staple rotating in the horizontal plane (FIGS. 7 and 10) during its forward travel. Once forming of the staple around the anvil is completed the forming force is removed from the former 52 by a drop-off in the cam, the anvil is lowered and the former advanced again to eject the staple from the device. During this forward movement (ejection phase), the sloped edges 52A and 52B of the former engage with the metal insert 160 to prise open the bullet section of the shaft assembly thus facilitating staple release.

Figure 3:
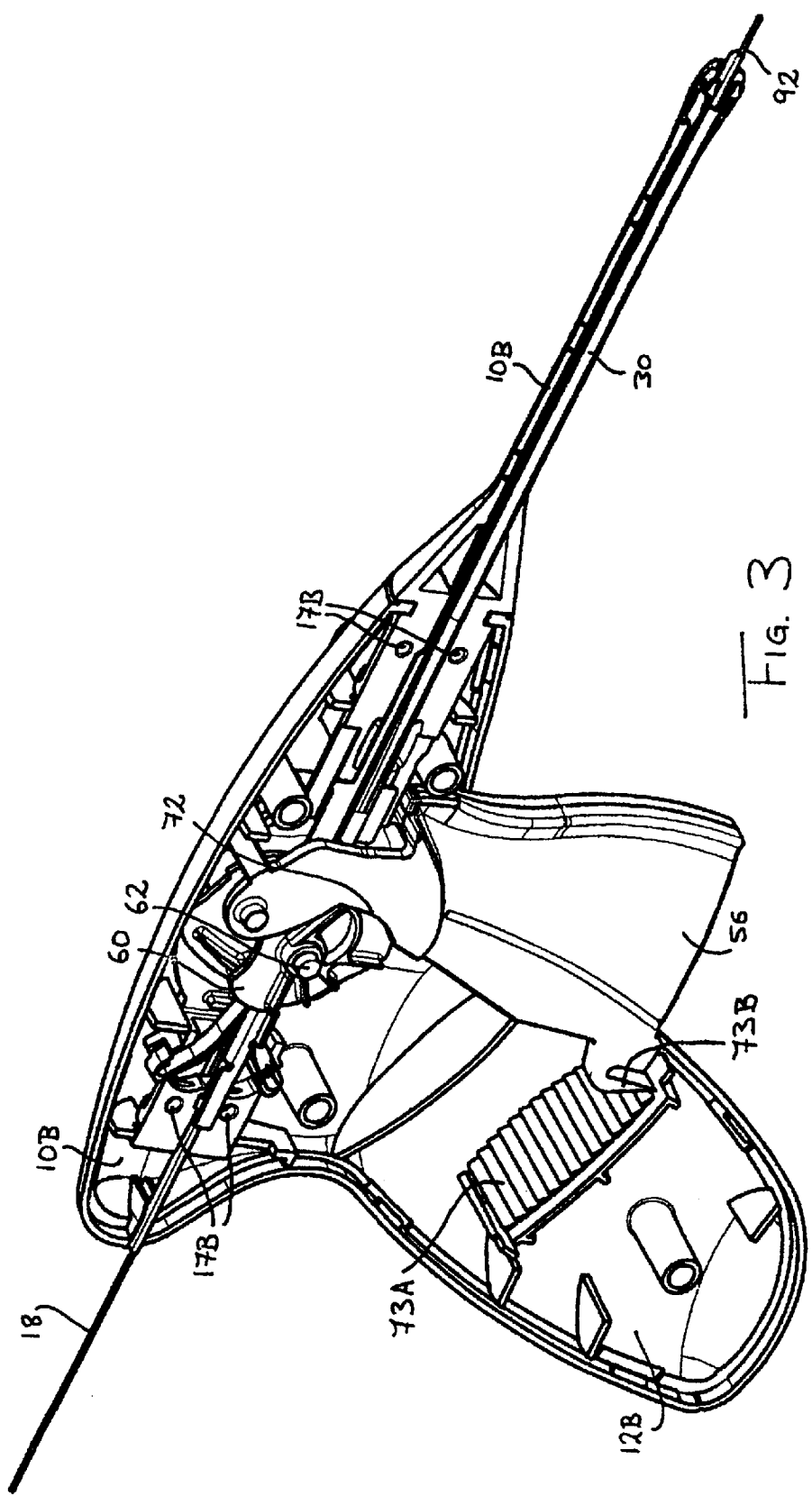
FIG. 3 is a perspective view of the stapler of FIG. 1 with the right hand side handle and shaft removed.
Figure 16:
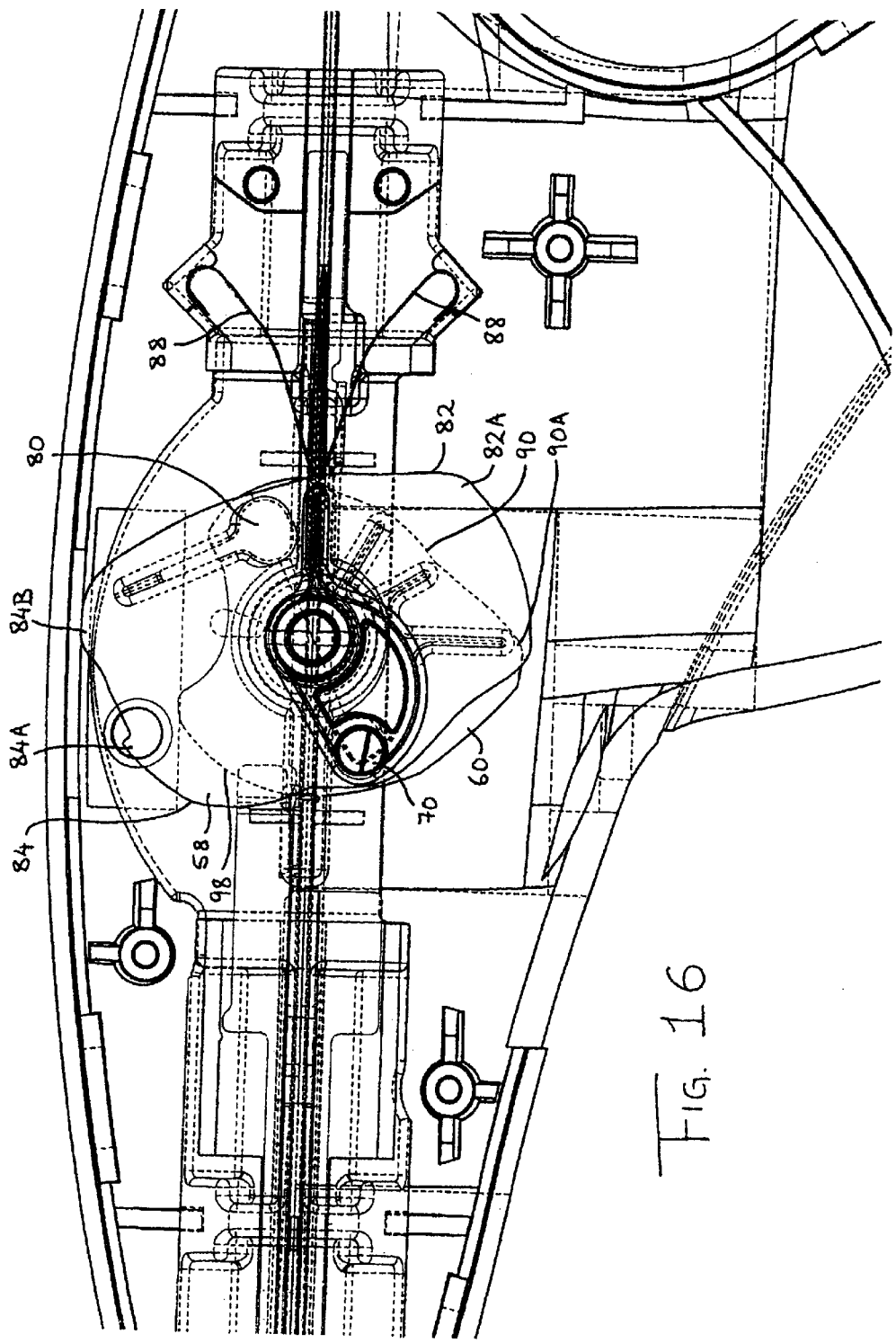
FIG. 16 is a side elevation of the cam mechanism.

The cam mechanism 62 can be seen in FIG. 3 and in enlarged views of FIGS. 15 and 16. The mechanism 62 consists of a first cam 58 and a second cam 60 mounted on a common axis 62 which sits in a recess 64 in the left-hand side 10A of the shaft (FIG. 4) and a corresponding recess (not shown) in the right-hand side 10B. Trigger 56 is similarly mounted in the shaft by a pair of stub axles 66 which are received in a trigger seating recess 68 in each half of the shaft 10, FIG. 4.

An actuating pin 70 extends through the first and second cams 58, 60. This actuating pin is acted on by a cam actuating surface 72 (FIG. 3) provided on the trigger 56, so that when the trigger is squeezed the actuating surface moves the actuating pin in an anti-clockwise direction around the axis 62. Because the actuating pin extends through both cams 58, 60 of the mechanism 62, the cams are both rotated simultaneously through the same angle as determined by the trigger squeeze. The use of this cam mechanism ensures accurate timing and positive mechanical displacements of all the moving components and accurate movement of the components relative to each other. The geometry of the trigger pivot pins 66 and actuating surface 72 relative to the cam pivot 62 and cam actuating pin 70 is configured to minimise the trigger rotation to only 23 degrees whilst the cam rotates a total of 90 degrees. This configuration also provides a mechanical advantage that the trigger delivers to the cam-actuating pin 70 of approximately 1:4. This geometry is further configured to deliver the best mechanical advantage at the phase during the staple forming cycle, which requires the highest forming forces, having the advantage of minimising the trigger effort and ensuring a constant trigger effort over the full cycle. Trigger 56 further comprises a ratchet lever 73B, shown in FIG. 3, which engages with ratchet strip 73A, which is mounted in the right handle 12A, FIG. 3. This non-return ratchet system ensures the firing cycle of the staple is uninterrupted, non-repeatable and provides a positive indication that the device has been used.

Referring back to FIG. 3, a leaf spring 88 positioned in a recess in the left-hand side 10A of the shaft and a corresponding recess (not shown) in the right hand side 10B. The free ends of the spring are formed into a loop so as to pivot freely in the curved corner recesses in which it sits and to aid assembly. The apex of this spring is positioned in a slot 74 in the crimped portion 94 of the blood locator tube 92 thus assuming the role of cam follower for the blood locator tube. This blood locator tube cam follower 74 is acted on by the first cam 58. Similarly, the first cam 58 acts on a former cam follower 76, whereas the second cam 60 acts on anvil-support cam followers 78A and 78B. The shape of the first and second cams 58, 60 are shown in elevation in FIG. 16 (the second cam 60 is shown in dotted outline as it is concealed by the first cam). FIG. 16 also shows actuating pin 70, and a reinforcing strut 80 mounted between the first and second cams diametrically opposite the actuating pin 70.

The cams are shown in the starting positions in FIGS. 15 and 16. Squeezing the trigger fully (through an angle of 23 degrees) causes the cams to rotate anti-clockwise through 90 degrees.

The apex of the leaf spring 88 which engages with and operates as a cam follower for the blood locator tube (leaf spring apex) acts against the rear surface 82 of the first cam 58. As the first cam rotates anti-clockwise from the position shown in FIG. 15, the distance between the blood locator tube cam follower 74 and the axis 62 is increased. This causes the blood locator tube to be drawn backwards as the trigger is squeezed.

The former cam follower 76 acts against the front surface 84 of the first cam 58. Again the distance between former cam follower 76 and axis 62 increases through the initial stages of the trigger being squeezed. The profile of surface 84 is designed with two distinct non-linear efficiencies, transitioned from low mechanical efficiency/high displacement to high mechanical efficiency/low displacement. The first rise rate being for displacement of the staple from its starting position to initial forming against the anvil, which requires the largest displacement of the staple with minimal load. The second non-linear rise rate is designed to correlate the cams mechanical efficiency with the load profile required to form the closed staple, minimising the trigger effort required and ensuring a constant trigger effort over the full cycle. A V-shaped section 84A of front section 84 causes the former 52 to momentarily suspend its forward motion when the staple has been fully formed. The effect of this is to momentarily release the pressure off the formed staple against the anvil, allowing the anvil to be dropped. The geometry of the distal tip of the former is designed to provide sufficient intrinsic spring tension to allow the forming arms 54 to further squeeze the formed staple, once the anvil has dropped, to further closed the formed staple. As the cam continues to rotate the raised profile 84B on the cam causes the former to advance forward again, ejecting the staple clear of the device.

It can be seen that a raised hump 82A on the profile of the rear surface 82 of the first cam is located almost diametrically opposite the V-shaped section 84A. The reason for this is to increase the rate at which the blood locator tube is drawn out of the puncture site just before the staple is fully formed and released. The intention is to leave the tube in the puncture as late as possible to provide support for the walls of the blood vessel for as long as possible And also to ensure that the head of the device remains centred over the puncture hole. The blood locator tube 92 is biased forward by the blood locator tube leaf spring 88 which also maintains pressure between the apex of the spring and the rear surface 82 of the first cam 58.

The blood locator tube leaf spring 88 allows the locator tube to be displaced in a proximal direction (back into the shaft of the device) against the spring tension in the event that the locator tube meets any significant resistance during insertion of the device, to prevent unnecessary trauma to soft tissues, the vessel or its rear wall.

An example of where this is particularly useful is if the stapler is advanced too far into the vessel, so that the tip of the tube 92 meets the inner wall. The blood locator tube will then be displaced back into the shaft, and may be designed to protrude through the end of the handle housing to give a visual indication that the device has been inserted against the wall. Furthermore, the device may be designed so that the blood outlet port 93 on the tube 92 is brought out of registry with the blood exit port 50 in the handle housing when the tube is displaced backwards, so that the clinician will note the flow of blood ceasing when the tube meets the inner vessel wall in this way.

The cam mechanism 62, however, provides positive mechanical displacements for withdrawing the locator tube at the appropriate timing, to ensure there is no chance of the staple being formed whilst the locator tube is in a forward position and potentially interfering with the staple formation.

A further reason to leave the blood locator tube in the puncture hole as late as possible is that the continued retraction of the tube everts or turns outwards the opposed edges of the puncture wound and aids penetration of the staple legs into the arterial wall. Eversion of the edges of the puncture helps prevent thrombus formation within the vessel. Yet another reason to leave the blood locator tube in the puncture hole as late as possible is to ensure that the stapler head remains centered over the hole during the staple delivery process. When the locator tube is fully retracted, only the guidewire is left within the wound, and this will be easily retracted from the closed wound after the stapler has been removed from the puncture site.

The anvil-support cam follower 78B acts against the rear surface 90 of the second cam 60. It can be seen that this rear surface 90 provides the greatest increase in distance relative to the axis to the section 90A from about 60 to 90 degrees below the horizontal. The reason for this is that the anvil is maintained in place until the staple has been formed and the pressure on the former has been relaxed slightly to allow the anvil to drop. The anvil is maintained in place for the initial 60 degrees of rotation by the anvil-support cam follower 78A being in contact with cam surface 98 of cam 60, preventing the anvil-support 30 from moving from its starting position. The cam surface 98 for the first 60 degrees of cam rotation is at a constant distance from the cam axle 62 (in dwell).

In use, the stapler is initially in the "pre-fire" configuration shown in FIGS. 6 to 8. The front end of the blood locator tube 92 is in a fully forward position projecting beyond the free end of the bullet portion 14 of the shaft 10, the anvil-support 30 is in a fully forward position with its arms 36 extending under the anvil's support wings 25 ensuring the anvil fingers 24A are directly in front of the staple 40, the former 52 is in a fully retracted position away from the anvil fingers 24A, and the staple 40 is in its fully back position up against the forming arms 54.

In this configuration the external end of a previously positioned guidewire 18 is inserted into the hole 96A in the front end of the blood locator tube 92 and fed through the tube 92 until it exits a guidewire exit port at the rear of the housing 12. The stapler is now fed along the guidewire 18 until the tip 95 of the tube 92 enters the blood vessel lumen through the vessel's puncture hole. This is indicated by blood flowing out of the blood exit port 50 or, if present, the adapter 51. At this point the front end of the bullet portion 14 of the shaft 10 will be resting against the exterior wall of the blood vessel.

Now the trigger 56 is squeezed, causing the cams of the cam mechanism 62 to rotate through 90 degrees. As mentioned, the rear end of each of the blood locator tube 92, anvil-support 30 and former 52 are coupled to the cam mechanism via cam followers and the following coordinated movement of these components takes place as the cams rotate through 90 degrees.

(A).

0 degrees: Stapler in pre-fire configuration.

32 degrees: Former 52 forward sufficiently to clamp staple against anvil fingers 24A, blood locator tube begins to retract. At this point the staple legs will have punctured the wall of blood vessel, but the staple is not yet fully deformed.

50 degrees: Former 52 forward sufficiently to deform the staple legs around the anvil fingers 24A and close the staple on the puncture site: blood locator tube 42 fully retracted. At some point between 32 and 50 degrees, the blood locator tube will have withdrawn from between the staple legs in time to allow them to close. This should be left as late as possible to provide support for the walls of the blood vessel for as long as possible.

65 degrees: Clamp force released from staple (due to drop off in cam profile). Anvil support 30 starting to retract.

75 degrees: Anvil support 30 retracted sufficiently to act against anvil sloped tilt arms 24B. Anvil fingers 24A begin to drop.

83 degrees: Anvil support 30 fully retracted. Anvil fingers 24A dropped down to allow release of staple. Intrinsic tension in former arms 54 further closes the staple. Former 52 begins to move forward again to eject staple. Former 52 begins to interfere with the insert 160 to spread bullet portion 14 of the shaft to allow for clear staple release.

90 degrees: Former 52 fully forward; staple ejected from the device.

The use of cams in cam mechanism 62 ensures the accuracy of sequence and relative timing between events as well as ensuring positive mechanical displacements of all components.

Figure 17:
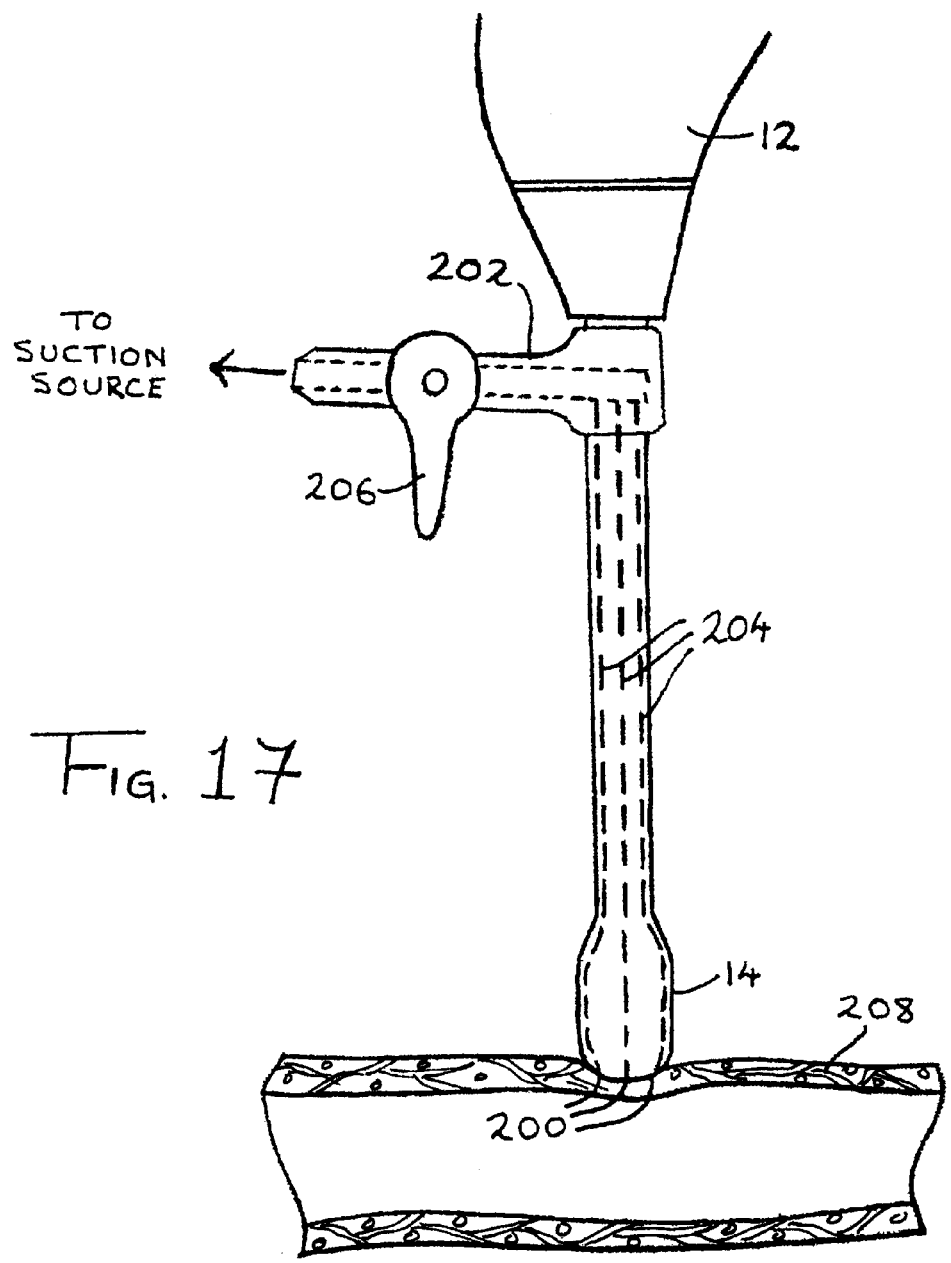
FIG. 17 is a side elevation of the shaft section of the device and suction port.

If desired, FIG. 17, the bullet head 14 of the shaft 10, which approximates the blood vessel wall 208, may include a number of suction ports 200. These ports are in communication with a suction adapter 202 via capillaries 204 within the shaft section. Suction, from a standard wall suction outlet or independent suction pump, is supplied to the suction adapter 202 via an on/off tap 206. Once the device is in position on the arterial wall, as indicated by blood flowing from the blood exit port, the tap 206 is turned to the "on" position thereby delivering suction to the ports 200 on the bullet head 14. This in turn suctions the blood vessel wall 208 against the face of the head 14 so as to stabilise it during delivery of the staple. Once delivered the suction is deactivated so as to remove the device from the blood vessel wall and tissue tract.

An alternative embodiment for the staple 40 is illustrated in FIGS. 20(A) and 20(B). In this case the centre portion 40C of the base section 40A is deformed in a generally 'U' shaped loop perpendicular to the common plane of the legs 40B which form an internal angle of between 70 and 85° with the base section 40A.

Another embodiment of staple is illustrated in FIGS. 21(A) and 21(B). The omega hump 40C is identical to that shown in FIG. 14. However, in this case, at the points A and B the outer ends 40A' of the base section are pre-bent backwardly to make an angle of between 130° and 150° with the inner ends 40A". The legs 40B extend forwardly from the outer ends 40A' of the base section and are substantially parallel to one another and perpendicular to a plane containing the omega section 40C and inner ends 40A" of the base section. The advantage of this configuration is that the rearwardly angled base section offers stability to the staple as it is advanced forward toward the anvil in the track formed between the top and bottom shaft. This prevents the legs tilting up or down as they advance beyond the free end of the shaft. In addition, once the staple is formed, FIG. 21B, the legs 40B are angled rearwardly toward the omega hump and away from the internal lumen of the vessel.

Another embodiment of staple is illustrated in FIGS. 22(A) and 22(B). The omega hump 40C is identical to that shown in FIG. 14. In this case, however, the inner ends 40A" of the base section are inclined back at between 30° and 50° from the plane of the omega section 40C. The base section includes the same pre-bends at points A and B between the base section inner and outer ends 40A", 40A' as shown in FIG. 14. The legs 40B extend forwardly from the outer ends 40A' of the base section and are substantially parallel to one another and perpendicular to a plane containing the omega section 40C. This construction offers the advantages of stability as the staple is advanced forward during firing, maximised closure from the pre-bend and, in the closed staple, legs 40B which are angled rearwardly toward the omega hump and away from the internal lumen of the vessel.

Figure 23A:
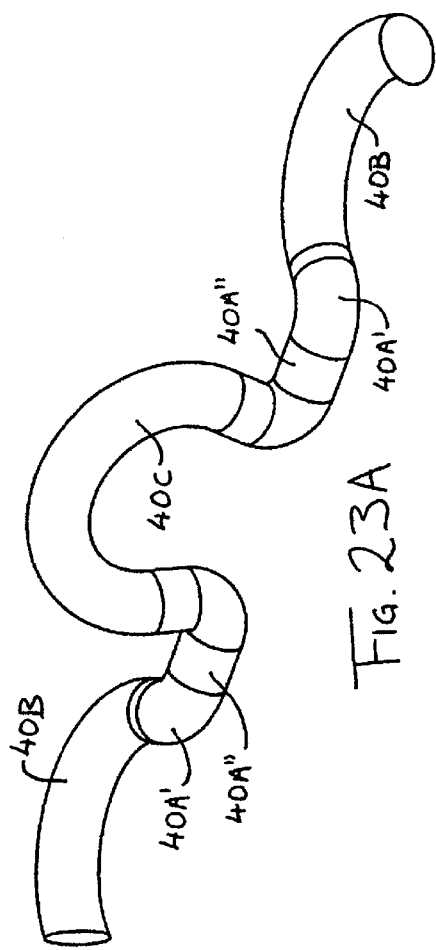
FIGS. 23(A) and (B) are pre- and post-fire views of a fifth embodiment of staple according to the invention.
Figure 23B:
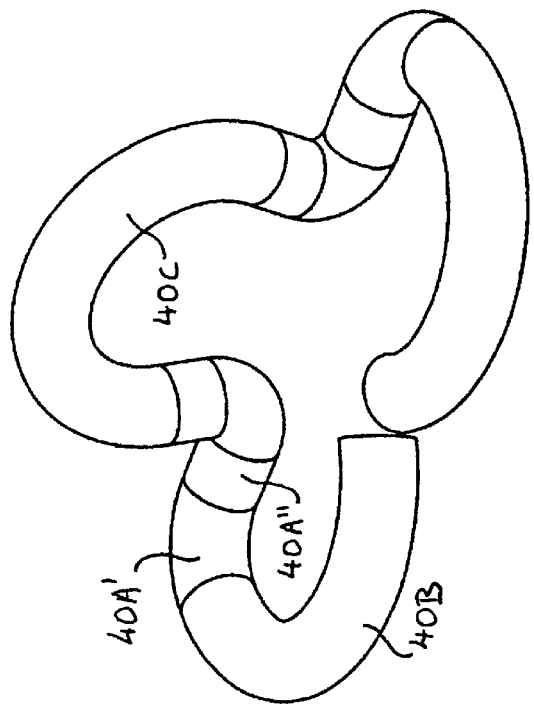

Yet another embodiment of staple is shown in FIGS. 23(A) and 23(B). In this case the outer ends 40A' of the base section and the respective legs 40B are combined to form one continuously curved element. The curved section begins at the point where the wire is intended to bend around the anvil and terminates at a pointed free end. The advantage of this curved base/legs is they again offer stability to the staple as it is advanced forward toward the anvil in that the pointed ends advance in a plane perpendicular to the omega section. Also, because of the curved nature of the base/leg the pointed end is always tending to advance into and across the puncture hole in the wall as opposed to advance through the wall and into the lumen and finally, after forming the leg points are facing away from the lumen and toward the hump section.

The embodiments shown herein have a loop which is substantially perpendicular to the common plane, although this need not be the case. The loop is preferably at an angle of at least 75 degrees from the common plane, as this enables it to lie close to e.g. an arterial wall when applied. For this reason a substantially perpendicular loop is preferred, but for design reasons a loop lying at any other angle could be employed provided that the staple can be properly deployed and that the loop does not cause unnecessary trauma when applied.

Obviously, features such as the bruise and pre-bend points can be applied to any of the embodiments shown above. While the illustrations show staples fabricated from round section wire the invention is not restricted to this. Other profiles such as rectangular, square, triangular, etc can be employed.

Furthermore, the staple need not be symmetrical about the loop, i.e. the base section and/or the legs can be different on the left-hand side and right-hand side. This may be particularly desirable where the staple is applied at an angle to the tissue wall and thus each leg is required to travel a different distance or to be deformed in a different shape to accomplish an optimal closure.

The invention is not limited to the embodiments described herein and may be modified or varied without departing from the scope of the invention.

What is claimed is:

1. A surgical staple comprising a base portion and a respective leg extending at an angle from each end of the base portion and terminating at a free end, the base portion and the legs lying in substantially a common plane except for a center portion of the base portion which is deformed in a loop at an angle to the common plane, the base portion being deformable at a weakened portion between each leg and the center portion to bring the free ends of the legs together to penetrate a liquid-carrying vessel at the site of a puncture and hold the opposite edges of the puncture together.

2. The surgical staple of claim 1, wherein the loop is generally U-shaped.

3. The surgical staple of claim 1, wherein the loop is generally omega-shaped.

4. The surgical staple of claim 3, wherein each leg extends at an angle from the respective end of the base portion, the legs pointing at least approximately in the same direction.

5. The surgical staple of claim 4, wherein the legs are substantially parallel.

6. The surgical staple of claim 4, wherein the legs converge at a small angle.

7. The surgical staple of claim 6, wherein on each side of the loop an outer end of the base portion is pre-bent at a small angle relative to an inner end of the base portion.

8. The surgical staple of claim 7, wherein the outer end is bent in the opposite direction to the direction in which the legs point.

9. The surgical staple of claim 7, wherein the outer end is bent in the same direction as the direction in which the legs point.

10. The surgical staple of claim 9, wherein the loop lies in a plane at an angle of at least 75 degrees to the common plane.

11. The surgical staple of claim 9, wherein the loop lies in a plane substantially perpendicular to the common plane.

12. The surgical staple of claim 9, wherein the legs form a continuous curve with the outer end of the base portion.

13. The surgical staple of claim 9, wherein the base portion is deformed to encourage bending between the outer end and the inner end during closure of the staple.

14. A surgical staple comprising a base portion and a respective leg extending from each end of the base portion and terminating at a free end, the base portion and the legs lying in substantially a common plane except for a center portion of the base portion which is deformed in a single loop at an angle to the common plane, the base portion having a configuration extending between the center portion and each leg selected from the group consisting of substantially straight, slightly curved, and slightly bent, and the base portion being deformable at a point between each leg and the center portion to bring the free ends of the legs together to penetrate a liquid-carrying vessel at the site of a puncture and hold the opposite edges of the puncture together.

15. The surgical staple of claim 14, wherein the loop is generally U-shaped.

16. The surgical staple of claim 14, wherein the loop is generally omega-shaped.

17. The surgical staple of claim 16, wherein each leg extends at an angle from the respective end of the base portion, the legs pointing at least approximately in the same direction.

18. The surgical staple of claim 17, wherein the legs are substantially parallel.

19. The surgical staple of claim 17, wherein the legs converge at a small angle.

20. The surgical staple of claim 19, wherein on each side of the loop an outer end of the base portion is pre-bent at a small angle relative to an inner end of the base portion.

21. The surgical staple of claim 20, wherein the outer end is bent in the opposite direction to the direction in which the legs point.

22. The surgical staple of claim 20, wherein the outer end is bent in the same direction as the direction in which the legs point.

23. The surgical staple of claim 22, wherein the loop lies in a plane at an angle of at least 75 degrees to the common plane.

24. The surgical staple of claim 22, wherein the loop lies in a plane substantially perpendicular to the common plane.

25. The surgical staple of claim 22, wherein the legs form a continuous curve with the outer end of the base portion.

26. The surgical staple of claim 22, wherein the base portion is deformed to encourage bending between the outer end and the inner end during closure of the staple.

27. A method of stapling closed a puncture site in a liquid-carrying vessel in a human or animal body, comprising the steps of:

introducing a stapling mechanism to the location of the vessel;

positioning the stapling mechanism at the puncture site by means of an elongated locator device associated with the stapling mechanism, the locator device sensing the position of the puncture site by entering the vessel at the site; and delivering a staple to, and deforming the staple to close, the puncture site;

wherein the staple comprises a base portion and a respective leg extending from each end of the base portion and terminating at a free end, the base portion being deformable to bring the free ends of the legs together to penetrate a blood vessel at the site of a puncture and hold the opposite edges of the puncture together, the base portion and legs lying in substantially a common plane except for a center portion of the base portion which is deformed into a single U-shaped member at an angle to the common plane; and wherein during delivery of the staple to the puncture site the single U-shaped member of the staple straddles and slides along the locator device.

* * * * *